(12) United States Patent
Maitro-Vogel et al.

(10) Patent No.: US 10,323,107 B2
(45) Date of Patent: Jun. 18, 2019

(54) ALKOXYLATES OF S-VINYLTHIOALKANOLS

(71) Applicant: BASF SE, Ludwigshafen (DE)

(72) Inventors: Sophie Maitro-Vogel, Mannheim (DE); Martin Ernst, Heidelberg (DE); Christian Schade, Ludwigshafen (DE); Pavel Tuzina, Mannheim (DE); Hoang Trang Tran-Thien, Paderborn (DE); Eva-Maria Reis-Walther, Breuberg (DE); Natalia Shabelina, Mannheim (DE); Nina Susanne Hillesheim, Nidda (DE); Christian Scholz, Wald a. d. Alz (DE)

(73) Assignee: BASF SE, Ludwigshafen (DE)

( * ) Notice: Subject to any disclaimer, the term of this patent is extended or adjusted under 35 U.S.C. 154(b) by 262 days.

(21) Appl. No.: 15/032,916

(22) PCT Filed: Oct. 30, 2014

(86) PCT No.: PCT/EP2014/073281
§ 371 (c)(1),
(2) Date: Apr. 28, 2016

(87) PCT Pub. No.: WO2015/063194
PCT Pub. Date: May 7, 2015

(65) Prior Publication Data
US 2016/0264691 A1 Sep. 15, 2016

(30) Foreign Application Priority Data
Oct. 30, 2013 (EP) ..................... 13190787

(51) Int. Cl.
*C04B 24/32* (2006.01)
*C07C 323/14* (2006.01)
(Continued)

(52) U.S. Cl.
CPC .............. *C08F 28/04* (2013.01); *C04B 24/16* (2013.01); *C04B 24/165* (2013.01); *C04B 24/32* (2013.01);
(Continued)

(58) Field of Classification Search
CPC ...................................................... C08F 28/04
See application file for complete search history.

(56) References Cited

U.S. PATENT DOCUMENTS

| | | | |
|---|---|---|---|
| 2,806,838 A * | 9/1957 | Melamed ........... | C07D 295/205 525/353 |
| 3,000,690 A | 9/1961 | Murdoch et al. | |
| 2004/0259982 A1 | 12/2004 | Bair et al. | |
| 2005/0009959 A1 | 1/2005 | Bair et al. | |
| 2007/0270547 A1 | 11/2007 | Bair et al. | |

FOREIGN PATENT DOCUMENTS

| | | |
|---|---|---|
| DE | 2058 120 A1 | 5/1972 |
| DE | 43 25 237 A1 | 2/1995 |
| DE | 10243361 A1 | 4/2004 |
| WO | WO 93/06142 A1 | 4/1993 |
| WO | WO 94/04580 A1 | 3/1994 |
| WO | WO 02/066528 A2 | 8/2002 |
| WO | WO 2005/000922 A1 | 1/2005 |
| WO | WO 2005/005500 A1 | 1/2005 |
| WO | WO 2009/040042 A1 | 4/2009 |
| WO | WO 2009/100956 A2 | 8/2009 |

OTHER PUBLICATIONS

International Search Report dated Nov. 18, 2014 in PCT/EP2014/073281.
Office Action dated Oct. 12, 2018 in Korean Patent Application No. 10-2016-7014447, citing document AA therein, 4 pages (with English language translation).

* cited by examiner

*Primary Examiner* — Wenwen Cai
(74) *Attorney, Agent, or Firm* — Oblon, McClelland, Maier & Neustadt, L.L.P.

(57) ABSTRACT

Unsaturated compounds of formula (I):

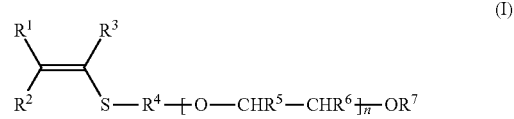

wherein: $R^1$, $R^2$, and $R^3$ are each independently H or $CH_3$; $R^4$ is a linear or branched $C_1$-$C_{30}$-alkylene; $R^5$ and $R^6$ are each independently H, $C_1$-$C_{20}$-alkyl, $C_3$-$C_{15}$-cycloalkyl, aryl, —$CH_2$—O—$C_1$-$C_{20}$-alkyl, or —$CH_2$—O—$C_2$-$C_{20}$-alkenyl, where $R^5$ and $R^6$ may together form a $C_3$-$C_6$-alkylene; $R^7$ is independently H, $C_1$-$C_4$-alkyl, or

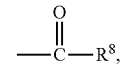

where $R^8$ is $C_1$-$C_{22}$-alkyl or $C_2$-$C_{22}$-alkenyl; and n is an integer from 2 to 200. Mixtures and polymers including the unsaturated compounds of formula (I). A method for preparing polymers by free-radical polymerization of monomers including the unsaturated compounds of formula (I). A process for preparing polymers including polymer-analogous reactions. And polymers including compounds (I) as cement additives, grinding aids, hydraulic binder additives, concrete plasticizers, reactive plasticizers for preparing plastics, rubber, or latex, associative thickeners and antioxidants, or for preparing polyether siloxanes.

39 Claims, No Drawings

(51) Int. Cl.
*C08F 28/04* (2006.01)
*C08F 220/06* (2006.01)
*C08F 228/02* (2006.01)
*C04B 24/16* (2006.01)
C04B 103/30 (2006.01)
C04B 103/52 (2006.01)

(52) U.S. Cl.
CPC .......... *C07C 323/14* (2013.01); *C08F 220/06* (2013.01); *C08F 228/02* (2013.01); C04B 2103/30 (2013.01); C04B 2103/52 (2013.01)

ALKOXYLATES OF S-VINYLTHIOALKANOLS

The present invention relates to alkoxylates of S-vinylthioalkanols and polymers comprising such alkoxylates of S-vinylthioalkanols as monomers. The invention further provides methods for preparing polymers comprising alkoxylates of S-vinylthioalkanols as monomers. The invention further relates to the uses of such polymers and mixtures comprising such polymers.

Further embodiments of the present invention can be inferred from the claims, the description and the examples. It will be appreciated that the features of the inventive subject matter which have been mentioned above and those which are still to be explained below can be used not only in the combination specified in each case but also in other combinations, without leaving the scope of the invention. Preferred and very preferred are especially also those embodiments of the present invention in which all features of the inventive subject matter have, respectively, the preferred and very preferred definitions.

WO 93/06142 A1 relates to copolymers of hydroxyalkylvinyl ethers, addition products of C2- to C4-alkylene oxides of hydroxyalkylvinyl ether and/or polytetrahydrofuran vinyl ether and optionally other copolymerizable monomers.

Copolymers are described in WO 94/04580 A1, which are prepared by polymerization of water-soluble, ethylenically unsaturated monomers containing acidic groups and monomers comprising a polyalkoxy sequence. The copolymers may comprise further monomers.

WO 02/066528 A2 describes alkoxylated acrylate and methacrylate macromonomers, which may be used as additives in concrete. Copolymers of macromonomers with other monomers such as acrylic acid, methacrylic acid or maleic acid are also mentioned in WO 02/066528 A2.

A dispersant for cement compositions is described in WO 2005/000922 A1, which comprises, inter alia, alkoxylated allyl alcohol sulfates and optionally other alkoxylated allyl alcohol groups as monomers.

WO 2005/005500 A1 relates to water-soluble or water-dispersible polymers comprising alkoxylated diallylamine derivatives, ethylenically unsaturated mono- or dicarboxylic acids, anhydrides thereof or mixtures thereof and optionally one or more further ethylenically unsaturated monomers. These polymers are used, inter alia, as additives in mineral building materials.

WO 2009/040042 A1 describes polycarboxylate ethers, which are suitable for use as concrete plasticizers or dispersants for inorganic pigments.

DE 20 58 120 discloses 2-hydroxyethyl vinyl sulfide, or derivatives thereof, comprising cationic polymers which are prepared by means of a two-stage process. In a first step, 2-hydroxyethyl vinyl sulfide, optionally together with comonomers such as acrylates, is polymerized. The resulting (co)polymers are reacted with alkylating agents in a second step, wherein the sulfur atoms are alkylated forming sulfonium groups. The alkylating agents used may be alkyl sulfates such as dimethyl sulfate, alkyl halides or alkylene oxides, although when using alkylene oxides inorganic or organic acids must be used in equimolar amounts.

Some problems occur in the preparation of polymers in the prior art. Allyl alcohol ethoxylates, for example, during polymerization or copolymerization, do not show particularly high reactivity and also give rise to some side reactions. Isoprenol ethoxylates are also not very reactive and this can lead to the formation of isoprene in the preparation process. Some of the alkoxylates, hydroxybutyl vinyl ether ethoxylates (HBVE ethoxylates) for example, have only limited stability to hydrolysis, particularly in acidic media.

It was an object of the present invention to provide polymers which do not have the disadvantages mentioned above. A part of the object of the invention was to develop reactive alkoxylate monomers for an efficient polymerization reaction. A further part of the object of the present invention is to provide such alkoxylate monomers having an increased stability to hydrolysis, both as monomers and copolymerized into the polymer.

These and other objects are achieved by the various embodiments of the invention, as is evident from the disclosure content of the present invention, in particular by unsaturated compounds of the general formula (I)

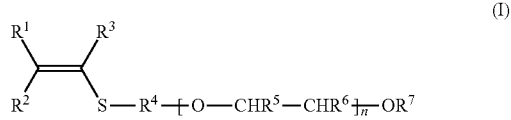

where
$R^1$, $R^2$, $R^3$ are the same or different and are each independently H, $CH_3$, preferably H,
R4 is a linear or branched $C_1$-$C_{30}$-alkylene, preferably a $C_2$-$C_{10}$-alkylene, particularly preferably a $C_2$-$C_4$-alkylene, particularly —$CH_2$—$CH_2$—,
$R^5$, $R^6$ are the same or different and are each independently, H, $C_1$-$C_{20}$-alkyl, $C_3$-$C_{15}$-cycloalkyl, aryl, $CH_2$—O—$C_1$-$C_{20}$-alkyl, $CH_2$—O—$C_2$-$C_{20}$-alkenyl, where $R^5$ and $R^6$ also may together form a $C_3$-$C_6$-alkylene, preferably may form tetramethylene,
preferably H, —$CH_3$, —$CH_2$—$CH_3$, —$C_3$-$C_{11}$-alkyl, $C_{12}$-$C_{22}$-alkyl, phenyl, $CH_2$—O—$C_1$-$C_{10}$-alkyl, $CH_2$—O—$C_2$-$C_{10}$-alkenyl,
particularly preferably H, —$CH_3$, —CH2-O—CH2-CH=CH2, —$CH_2$—O-2-ethylhexyl, more preferably H or —$CH_3$ and especially preferably H, $R^7$ is the same or different and is independently H, $C_1$-$C_4$-alkyl or

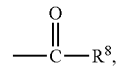

preferably H or $C_1$-$C_4$-alkyl, particularly preferably H,
$R^8$ is $C_1$-$C_{22}$-alkyl, $C_2$-$C_{22}$-alkenyl,
preferably $C_{12}$-$C_{18}$-alkyl, $C_{12}$-$C_{18}$-alkenyl,
n is an integer from 2 to 200, particularly from 2 to 160, preferably from 5 to 140, particularly preferably 10 to 80 and, for example, 20 to 30.

For the purposes of this invention, expressions of the form $C_a$—$C_b$ refer to chemical compounds or substituents with a specific number of carbon atoms. The number of carbon atoms can be selected from the entire range from a to b, including a and b, a is at least 1 and b is always greater than a. The further specification of the chemical compounds or of the substituents takes place through expressions of the form $C_a$—$C_b$—V. V here is a chemical compound class or substituent class, for example alkyl compounds or alkyl substituents.

Specifically, the collective terms specified for the different substituents are defined as follows:

$C_1$-$C_{22}$-alkyl: straight-chain or branched hydrocarbon residues having up to 22 carbon atoms, for example $C_1$-$C_{10}$-alkyl or $C_{11}$-$C_{22}$-alkyl, preferably $C_1$-$C_{10}$-alkyl, for example $C_1$-$C_3$-alkyl such as methyl, ethyl, propyl, isopropyl, or $C_4$-$C_6$-alkyl, n-butyl, sec-butyl, tert-butyl, 1,1-dimethylethyl, pentyl, 2-methylbutyl, 1,1-dimethylpropyl, 1,2-dimethylpropyl, 2,2-dimethylpropyl, 1-ethylpropyl, hexyl, 2-methylpentyl, 3-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 2-ethylbutyl, 1,1,2-trimethylpropyl, 1,2,2-trimethylpropyl, 1-ethyl-1-methylpropyl, 1-ethyl-2-methylpropyl, or $C_7$-$C_{10}$-alkyl, such as heptyl, octyl, 2-ethylhexyl, 2,4,4-trimethylpentyl, 1,1,3,3-tetramethylbutyl, nonyl or decyl and isomers thereof.

$C_2$-$C_{20}$-alkenyl: unsaturated, straight-chain or branched hydrocarbon residues having 2 to 20 carbon atoms and one, two or three, preferably one, double bonds in any desired position, for example, $C_2$-$C_{10}$-alkenyl or $C_{11}$-$C_{20}$-alkenyl, preferably $C_2$-$C_{10}$-alkenyl, for example $C_2$-$C_4$-alkenyl, such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, or $C_5$-$C_6$-alkenyl, such as 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-petetenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl or 1-ethyl-2-methyl-2-propenyl, and also $C_7$-$C_{10}$-alkenyl, such as the isomers of heptenyl, octenyl, nonenyl or decenyl.

$C_1$-$C_{30}$-alkylene: straight-chain or branched hydrocarbon residues having 1 to 30 carbon atoms, for example, $C_1$-$C_{10}$-alkylene or $C_{11}$-$C_{20}$-alkylene, preferably $C_1$-$C_{10}$-alkylene, particularly methylene, dimethylene, trimethylene, tetramethylene, pentamethylene or hexamethylene.

$C_3$-$C_{15}$-cycloalkyl: monocyclic, saturated hydrocarbon groups having 3 to carbon ring members, preferably $C_3$-$C_8$-cycloalkyl such as cyclopropyl, cyclobutyl, cyclopentyl, cyclohexyl, cycloheptyl or cyclooctyl and also a saturated or unsaturated cyclic system such as norbornyl or norbenyl, for example.

Aryl: a mono- to tricyclic aromatic ring system comprising from 6 to 14 carbon ring members, for example phenyl, naphthyl or anthracenyl, preferably a mono- to bicyclic, more preferably a monocyclic, aromatic ring system.

In a particularly preferred embodiment of the invention, the unsaturated compounds (I) are those of the general formula (Ia)

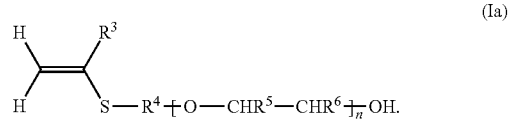

In the formula (Ia), $R^3$ is H or methyl, preferably H, $R^4$ is a linear or branched $C_2$-$C_{10}$-alkylene group, preferably a linear $C_2$-$C_{10}$-group, particularly a linear or branched, preferably a linear $C_2$-$C_4$-alkylene group. Examples include 1,2-ethylene, 1,3-propylene and 1,4-butylene groups, and $R^4$ is especially preferably a 1,2-ethylene group —$CH_2CH_2$—.

The group -[—O—$CHR^5$—$CHR^6$—]$_n$- in formula (Ia) is a polyalkoxy group comprising n —O—$CHR^5$—$CHR^6$— alkoxy groups, wherein the alkoxy groups may each be the same or different. $R^5$ and $R^6$ are each independently H, methyl or ethyl, preferably H or methyl and especially H, with the proviso that the sum total of carbon atoms in the $R^5$ and $R^6$ residues per alkoxy group is in each case 0 to 2. In other words, the polyalkoxy group thus comprises groups selected from the groups of ethoxy, propoxy and butoxy groups. If different alkoxy groups are present, these may be arranged in any desired sequence, for example, randomly, alternating or in blocks. In a preferred embodiment, at least 50 mol %, preferably at least 80% of the alkoxy groups are ethoxy groups. Particularly preferably they are exclusively ethoxy groups, i.e. $R^5$ and $R^6$ are H.

In formula (Ia), n is a number from 2 to 200, preferably 5 to 160, particularly preferably 10 to 140, especially preferably 20 to 140 and, for example, 20 to 30.

In a further preferred embodiment of the invention, the unsaturated compounds (I) are those of the general formula (Ib)

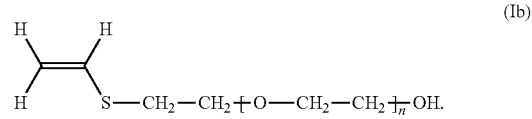

where n is a number from 2 to 200, preferably 5 to 160, particularly preferably 10 to 140, especially preferably 20 to 140 and, for example, 20 to 30.

The compounds (I), particularly the compounds of formula (Ia), can be prepared in particular by alkoxylation of unsaturated compounds of the general formula (II)

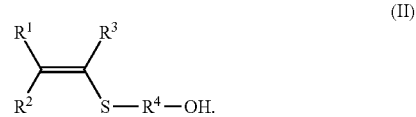

For this purpose, the compound (II) is reacted with the desired amount of alkylene oxides or alkylene ether oxides, in particular $C_2$- to $C_4$-alkylene oxides, particularly preferably ethylene oxide.

The performance of an alkoxylation is known in principle to those skilled in the art. In this case, it is regularly recommended to avoid acids as catalysts for the alkoxylation. In a preferred embodiment of the invention, the alkoxylation is a base-catalyzed alkoxylation. To this end, the compound (II) used as the starting material can be admixed in a pressure reactor with basic catalysts, particularly alkali metal hydroxides, preferably potassium hydroxide, or with alkali metal alkoxides, for example potassium methoxide.

However, the alkoxylation may also be carried out by other methods. For example, it is possible to use double hydroxide clays, as described in DE 4325237 A1, or it is possible to use double metal cyanide catalysts (DMC catalysts). Suitable DMC catalysts are disclosed, for example, in DE 10243361 A1, especially in paragraphs [0029] to [0041] and the literature cited therein. For example, it is possible to use catalysts of the Zn—Co type. To perform the reaction, the alcohol $(R^1)(R^2)$—CH—$CH_2$—OH can be admixed with the catalyst, and the mixture can be dewatered as described above and reacted with the alkylene oxides as described. Typically not more than 1000 ppm of catalyst based on the mixture are used, and the catalyst can remain in the product owing to this small amount. The amount of catalyst may generally be less than 1000 ppm, for example 250 ppm or less.

The present invention further relates to mixtures comprising compounds of the general formula (I), preferably of the general formula (Ia), particularly preferably of the general formula (Ib). The amount of compounds of the general formula (I) in such mixtures may vary over a wide range, depending on the end use of the mixtures. The amount of compounds of the general formula (I) in such mixtures is generally from 1 to 99% by weight, preferably 10 to 95% by weight, based on the total amount of the mixture.

Such mixtures can be, for example, mixtures of compounds different from one another of the general formula (I), preferably of the general formula (Ia), particularly preferably of the general formula (Ib). Furthermore, they can be mixtures, for example with solvents, other monomers and/or further additives such as stabilizers for preventing the polymerization, surfactants and/or other admixtures and additives.

In a preferred embodiment of the invention, such mixtures are aqueous solutions of the compounds of the general formula (I). One advantage of such aqueous solutions of the compounds of the general formula (I) is easy handling, particularly during metering.

The present invention further relates to polymers comprising as monomers compounds of the formula (I), preferably those of the formula (Ia), particularly preferably those of the general formula (Ib). Said polymers can be homopolymers of the compounds (I) or copolymers comprising compounds (I).

In a preferred embodiment of the invention, the polymers according to the invention comprise at least one further monomer (further monomer), different from the compounds of the general formula (I). Multiple monomers different from the compounds of the general formula (I) may also evidently be present in the polymer.

The at least one further monomer is particularly preferably a monoethylenically unsaturated monomer.

Suitable further monomers are $C_2$-$C_{24}$ alkenes, for example ethene, propene, 1-butene, 2-butene, isobutene, diisobutene, 1-hexene, 1-heptene, 1-octene, 1-nonene, 1-decene, 1-dodecene, 1-octadecene.

Suitable further monomers are also conjugated $C_4$-$C_{10}$ dienes, for example, butadiene, isoprene or chloroprene.

The further monomers, particularly monoethylenically unsaturated further monomers, may particularly be monomers comprising acid groups, where the acid groups may also be completely or partly neutralized. These may particularly take the form of alkali metal salts, alkaline earth metal salts, ammonium salts or salts of organic ammonium ions. Preference may be given to monomers comprising acid groups selected from the groups of carboxylic acid groups, sulfonic acid groups, phosphoric acid groups or phosphonic acid groups.

Examples of suitable further monomers having carboxylic acid groups comprise $C_3$-$C_{12}$ monoethylenically unsaturated mono- or dicarboxylic acids, anhydrides or salts thereof, such as acrylic acid, methacrylic acid, (meth)acrylic anhydride, crotonic acid, maleic acid, maleic anhydride, fumaric acid, itaconic acid, mesaconic acid, citraconic acid or methylene malonic acid and ammonium or alkali metal salts thereof. The acids may be used fully or partly in neutralized form.

Examples of suitable further monomers having phosphoric acid groups or phosphonic acid groups include monoethylenically unsaturated phosphonic esters or (poly)phosphoric esters and salts thereof, such as vinylphosphonic acid or esters of hydroxyethyl, hydroxypropyl or hydroxybutyl (meth)acrylate with (poly)phosphoric acid and alkali metal and ammonium salts thereof, monovinyl phosphate, allylphosphonic acid, monoallyl phosphate, 3-butenylphosphonic acid, mono-3-butenyl phosphate, mono(4-vinyloxybutyl) phosphate, mono(2-hydroxy-3-vinyloxypropyl) phosphate, mono(1-phosphonoxymethyl-2-vinyloxyethyl) phosphate, mono(3-allyloxy-2-hydroxypropyl) phosphate, mono[2-(allyloxy-1-phosphonoxymethylethyl)]phosphate, 2-hydroxy-4-vinyloxymethyl-1,3,2-dioxaphosphole, 2-hydroxy-4-allyloxymethyl-1,3,2-dioxaphosphole. It is also possible to use salts and/or esters, particularly $C_1$-$C_8$ mono-, di- and optionally trialkyl esters of monomers containing phosphoric acid and/or phosphonic acid groups.

Examples of further suitable monomers having sulfonic acid groups include monoethylenically unsaturated sulfonic acids and salts thereof such as vinylsulfonic acid, 2-acrylamido-2-methylpropanesulfonic acid, 2-acrylamidomethyldodecylsulfonic acid, 2-(meth)acryloxyethanesulfonic acid, 3-(meth)acryloxypropanesulfonic acid, allyloxybenzenesulfonic acid, vinylbenzenesulfonic acid, vinyltoluenesulfonic acid, allylsulfonic acid, methallylsulfonic acid and corresponding ammonium and alkali metal salts thereof.

Suitable further monomers are also esters, amides and imides of monoethylenically unsaturated mono- or dicarboxylic acids, particularly of the aforementioned monoethylenically unsaturated $C_3$-$C_{12}$ carboxylic acids, particularly $C_1$-$C_{40}$, preferably $C_1$-$C_{22}$, particularly preferably $C_2$-$C_{12}$ esters, amides or imides. The substituents may also bear further heteroatoms. Dicarboxylic acids here may also be present in the form of their monoesters or monoamides, for example as $C_1$-$C_4$ monoesters. The amides and imides may be present in N-mono- or, optionally, N,N-dialkylated form.

The esters may in particular be esters of (meth)acrylic acid, particularly (meth)acrylic esters with aliphatic or cycloaliphatic ester groups, in particular $C_1$-$C_{22}$, preferably $C_2$-$C_{12}$ ester groups. Examples of such compounds include methyl (meth)acrylate, ethyl (meth)acrylate, propyl (meth)acrylate, isopropyl (meth)acrylate, 1-butyl (meth)acrylate, isobutyl (meth)acrylate, tert-butyl (meth)acrylate, pentyl (meth)acrylate, isoamyl (meth)acrylate, hexyl (meth)acrylate, heptyl (meth)acrylate, isodecyl (meth)acrylate, lauryl (meth)acrylate, stearyl (meth)acrylate, behenyl (meth)acrylate, cyclohexyl (meth)acrylate, 4-tert-butylcyclohexyl (meth)acrylate, isobornyl (meth)acrylate, 2-ethylhexyl (meth)acrylate, 2-propylheptyl (meth)acrylate or citronellol (meth)acrylate.

The ester groups may also comprise heteroatoms, particularly oxygen and/or nitrogen atoms. Examples of such esters include hydroxyethyl (meth)acrylate, hydroxypropyl (meth) acrylate, hydroxybutyl (meth)acrylate, ethyldiglycol (meth) acrylate, hydroxypropylcarbamate (meth)acrylate, phenyl (meth)acrylate, benzyl (meth)acrylate, 2-phenylethyl (meth) acrylate, 3-phenylpropyl (meth)acrylate, ureido (meth)acrylate, acetoacetoxyethyl (meth)acrylate, hydroxyethylpyrrolidone (meth)acrylate, tert-butylaminoethyl (meth)acrylate, diethylaminoethyl (meth)acrylate and dimethylaminoethyl (meth)acrylate. Examples of preferred esters of (meth) acrylic acid include hydroxyethyl (meth)acrylate, hydroxypropyl (meth)acrylate and hydroxybutyl (meth)acrylate.

The alcohol components in the (meth)acrylic esters may be alkoxylated alcohols. Particularly of note here are alkoxylated $C_1$-$C_{18}$ alcohols having 2 to 80 mol of ethylene oxide, propylene oxide, butylene oxide or mixtures thereof. Examples of such alkoxylated products comprise methylpolyglycol (meth)acrylate or (meth)acrylic esters of $C_{13}$/$C_{15}$-oxoalcohol or mixtures thereof reacted with 3, 5, 7, 10 or 30 mol of ethylene oxide.

Further examples of esters, amides or imides include monoethyl maleate, diethyl maleate, dimethyl maleate, N-substituted maleic imides such as N-methyl-, N-phenyl- and N-cyclohexylmaleic imide, acrylamide, methacrylamide, N-methyl (meth)acrylamide, N,N-dimethyl (meth)acrylamide, N,N-diethylacrylamide, N-isopropyl (meth)acrylamide, N-methylol (meth)acrylamide, N-hydroxyethyl (meth)acrylamide, N-tert-butyl (meth)acrylamide, N-tert-octyl (meth)acrylamide, N-(1-methylundecyl) (meth)acrylamide, 10-acrylamidoundecanoic acid, N-cyclohexyl (meth) acrylamide, diacetone acrylamide, dimethylaminoethyl (meth)acrylamide, dimethylaminopropyl (meth)acrylamide, N,N-dimethyl-N-(meth)acrylamidopropyl-N-(3-sulfopropyl)ammonium betaine, (meth)acryloyl morpholine.

Monomers bearing amino or imino groups may also be present in protonated form or in the form of their quaternary salts, for example by quaternization with methyl chloride, dimethyl sulfate or diethyl sulfate. The monomers may also be present reacted with propane sultone to the corresponding betaines.

Further suitable monomers are also monomers comprising N-vinyl groups, for example, N-vinylpyrrolidone, N-vinylcaprolactam, N-vinyl-N-methylacetamide, N-vinylimidazole, 2-methyl-1-vinylimidazole, quaternary N-vinylimidazole derivatives, for example, 1-vinyl-3-methylimidazolium chloride or methosulfate, N-vinyl-1,2,4-triazole, N-vinylcarbazole, N-vinylformamide, 2-methyl-1-vinylimidazoline.

Further suitable monomers are $C_1$-$C_{24}$ esters of vinyl alcohol and monocarboxylic acids, for example, vinyl formate, vinyl acetate, vinyl propionate, vinyl n-butyrate, vinyl laurate, vinyl stearate, or vinyl esters of Koch acids, for example, of 2,2-dimethylpropanoic acid, 2,2-dimethylbutanoic acid, 2,2-dimethylpentanoic acid, 2-ethyl-2-methylbutanoic acid, neononanoic acid, neodecanoic acid.

Also suitable are vinyl or allyl ethers such as methyl vinyl ether, ethyl vinyl ether, propyl vinyl ether, isobutyl vinyl ether, tert-butyl vinyl ether, 2-ethylhexyl vinyl ether, vinyl cyclohexyl ether, vinyl 4-hydroxybutyl ether, decyl vinyl ether, dodecyl vinyl ether, octadecyl vinyl ether, hydroxybutyl vinyl ether, 2-(diethylamino)ethyl vinyl ether, 2-(di-n-butylamino)ethyl vinyl ether or methyldiglycol vinyl ether or the corresponding allyl compounds.

Also suitable are unsaturated alcohols such as 3-buten-1-ol, 2-buten-1-ol, allyl alcohol, isoprenol, prenol, methallyl alcohol.

Also suitable are alkoxylated vinyl, allyl, methallyl or isoprenyl ethers having 1-150 mol of EO units or mixtures of EO and PO units.

Further suitable monomers are also N-allyl compounds, for example, diallylamine, N,N-dimethyl-N,N-diallylammonium chloride.

Further suitable monomers are also α,β-monoethylenically unsaturated nitriles having 3 to 10 carbon atoms, for example, acrylonitrile, methacrylonitrile, fumaronitrile, maleonitrile.

Still further suitable monomers are vinyl aromatic monomers such as styrene, vinyl toluene or a-methylstyrene. Further styrene derivatives satisfy the general formula IV

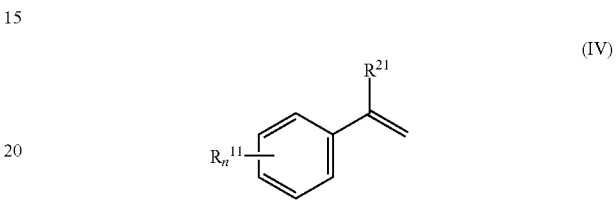

in which $R^{11}$ and $R^{21}$ are hydrogen or $C_1$-$C_8$-alkyl and n is equal to 0, 1, 2 or 3. The aromatic ring may also bear heteroatoms, for example, 2- and 4-vinylpyridine.

Still further suitable monomers are halogenated alkenes, for example, vinyl chloride, vinylidene chloride, trifluoroethylene, tetrafluoroethylene, and also acrolein, methacrolein.

The further monomers may also be crosslinking monomers.

Examples of further suitable crosslinking monomers comprise molecules having multiple ethylenically unsaturated groups, for example, di(meth)acrylates such as ethylene glycol di(meth)acrylate, butanediol-1,4-di(meth)acrylate or hexanediol di(meth)acrylate or poly(meth)acrylates such as trimethylolpropane tri(meth)acrylate, pentaerythritol tri (meth)acrylate or also di(meth)acrylates of oligo- or polyalkylene glycols such as di-, tri- or tetraethylene glycol di(meth)acrylate or di-, tri- or tetrapropylene glycol di(meth) acrylate. Further examples comprise divinylbenzene, divinylethylene urea, vinyl (meth)acrylate, allyl (meth)acrylate, isoprenyl (meth)acrylate, prenyl (meth)acrylate, dihydrodicyclopentadienyl acrylate, dicyclopentadienyl (meth)acrylate or butanediol divinyl ether. Also suitable are di- and oligo allyl or vinyl ethers of polyhydroxy compounds, for example ethylene glycol divinyl ether, butanediol divinyl ether, 1,4-cyclohexanedimethanol divinyl ether, diethylene glycol divinyl ether, triethylene glycol divinyl ether, pentaerythritol tri- or tetraallyl ether. Also suitable are oligoallylamines, for example, triallylamine or tetraallylammonium chloride. Also suitable are di- and oligoallyl esters of polycarboxylic acids, for example, diallyl phthalate, diallyl maleate, triallyl trimellitate, divinyl esters of dicarboxylic acids such as succinic acid and adipic acid. Also suitable are di-, tri- or oligo(meth)acrylamides, for example N,N'-methylene bis(meth)acrylamide. The content of crosslinking monomers is generally from 0 to 20 mol %, based on the total number of all monomers, preferably from 0 to 10 mol % and particularly preferably from 0 to 5 mol %, and especially preferably the polymers according to the invention do not comprise any crosslinking monomers.

Examples of preferred monoethylenically unsaturated further monomers include styrene, butadiene, methyl (meth) acrylate, ethyl acrylate, dibutyl maleate, methyl alpha-cyanoacrylate, acrylonitrile, acrylic acid, methacrylic acid, maleic acid (anhydride), itaconic acid, vinylphosphonic acid, N-vinylpyrrolidone, N,N-dimethyl-N,N-diallylammonium chloride, acrylamide, vinylimidazole, vinyl acetate, allylsulfonic acid, 2-acrylamido-2-methylpropanesulfonic acid, particular preference being given to acrylic acid, methacrylic acid, methyl (meth)acrylate, maleic acid (anhydride), (iso)prenyl alkoxylate, (meth)allyl alkoxylate or hydroxybutyl vinyl ether alkoxylate. Very particular preference is given to acrylic acid, methacrylic acid, (meth)acrylate, maleic acid (anhydride), (iso)prenyl alkoxylate, (meth)allyl alkoxylate or hydroxybutyl vinyl ether alkoxylate.

In a further preferred embodiment of the polymers according to the invention, at least one further monomer present in the polymer, different from the compounds of the general formula (I), is acrylic acid. With particular preference in this case, no other monomers are present besides unsaturated compounds of the general formula (I) and acrylic acid.

In a further preferred embodiment of the polymers according to the invention, at least one further monomer present in the polymer, different from the compounds of the general formula (I), is methacrylic acid. With particular preference in this case, no other monomers are present besides unsaturated compounds of the general formula (I) and methacrylic acid. The compounds of the general formula (I) according to the invention can be readily copolymerized with (meth)acrylic acid and derivatives thereof, in contrast to the corresponding vinyl ether compounds.

In a further preferred embodiment of the polymers according to the invention, at least one further monomer present in the polymer, different from the compounds of the general formula (I), is maleic acid (anhydride). With particular preference in this case, no other monomers are present besides unsaturated compounds of the general formula (I) and maleic acid (anhydride).

The polymers according to the invention may nevertheless evidently comprise low amounts of starters or regulators, even if they are prepared only from specific compounds of the general formula (I) as monomers and/or also from monomers different from the compounds of the general formula (I), due to the preparation method thereof.

In further preferred embodiments of the polymers according to the invention, no other monomers are present besides unsaturated compounds of the general formula (I), acrylic acid and methacrylic acid or acrylic acid and maleic acid (anhydride) or methacrylic acid and maleic acid (anhydride).

In a further preferred embodiment of the polymers according to the invention, no other monomers are present besides unsaturated compounds of the general formula (I), acrylic acid, methacrylic acid and maleic acid (anhydride).

The composition of the polymers according to the invention may vary over a wide range, depending on the particular end use. The person skilled in the art makes a suitable selection.

The polymers according to the invention generally comprise from 1 to 99.9% by weight, in particular from 5 to 99.9% by weight, preferably from 10 to 99.9% by weight, particularly preferably from 30 to 99.5% by weight, particularly preferably from 50 to 99% by weight and especially preferably from 55 to 96% by weight of unsaturated compounds of the general formula (I), in each case based on the total amount of monomers in the polymer.

In a preferred embodiment of the invention, the polymers according to the invention comprise from 1 to 99.9% by weight of unsaturated compounds of the general formula (I), preferably compounds (Ia), particularly preferably compounds (Ib) and also 99 to 0.1% by weight of monoethylenically unsaturated further monomers, preferably 10 to 99.9% by weight of compounds (I) and 90 to 0.1% by weight of monoethylenically unsaturated further monomers, particularly preferably from 30 to 99.9% by weight of compounds (I) and 70 to 0.1% by weight of monoethylenically unsaturated further monomers, based in each case on the total amount of monomers present, with the proviso that the total amount of compounds of the formula (I) and monoethylenically unsaturated further monomers is at least 80% by weight, preferably at least 90% by weight, particularly preferably at least 95% by weight. With very particular preference, no other monomers are present besides compounds of the formula (I) and monoethylenically unsaturated further monomers.

In a further preferred embodiment, the polymers according to the invention comprise from 1 to 99.9% by weight, preferably from 10 to 99.9% by weight, particularly preferably from 30 to 99.9% by weight of unsaturated compounds of the general formula (I), preferably compounds (Ia), particularly preferably compounds (Ib) and in total from 99 to 0.1% by weight, preferably from 90 to 0.1% by weight, particularly preferably 70 to 0.1% by weight of further monomers, where the amounts mentioned are in each case based on the total amount of monomers in the polymer, and in which the further monomers comprise at least one selected from the group of (1) monoethylenically unsaturated monomers comprising carboxylic acid groups or anhydrides or salts thereof, such as acrylic acid, methacrylic acid, maleic acid or maleic anhydride, (2) monoethylenically unsaturated monomers comprising phosphorus or phosphonic acid groups or salts thereof, such as esters of hydroxyethyl, hydroxypropyl or hydroxybutyl (meth)acrylate with (poly)phosphoric acid, (3) monoethylenically unsaturated monomers comprising sulfonic acid groups or salts thereof, such as vinylsulfonic acid or 2-acrylamido-2-methylpropanesulfonic acid, (4) hydroxyalkyl (meth)acrylates such as hydroxyethyl acrylate or hydroxypropyl acrylate, (5) monoethylenically unsaturated monomers comprising polyalkoxy groups such as (iso)prenyl alkoxylate, (meth)allyl alkoxylate, hydroxybutyl vinyl ether alkoxylate or (meth)acrylic acid alkoxylates.

In a further preferred embodiment, the polymer according to the invention comprises at least two further different monomers, in particular at least two further different monoethylenically unsaturated monomers, in addition to at least one compound (I), preferably (Ia), particularly preferably (Ib). The further monomers preferably take the form of at least one monoethylenically unsaturated monomer comprising acid groups, preferably a monomer selected from the groups (1), (2) and (3) described above and also a monoethylenically unsaturated monomer comprising OH groups and/or polyalkoxy groups, preferably a monomer selected from the groups (4) and (5) described above.

In this preferred embodiment, the amount of compounds (I), preferably compounds (Ia), particularly preferably compounds (Ib) is generally 1 to 99.9% by weight, preferably from 10 to 99.9% by weight, particularly preferably from 30 to 99.9% by weight and the amount of the two further monomers together is 99 to 0.1% by weight, preferably from 90 to 0.1% by weight, particularly preferably 70 to 0.1% by weight, in each case based on the total amount of all monomers in the polymer.

In a preferred embodiment of the invention, the polymer according to the invention comprises 70 to 99% by weight, preferably 80 to 98% by weight of at least one compound (Ib) and also 1 to 30% by weight, preferably 2 to 20% by weight of (meth)acrylic acid.

The polymers according to the invention, depending on the composition, have molar mass distributions which may vary over a wide range. The person skilled in the art chooses a suitable molar mass depending on the intended use of the polymer. The number-average molar mass Mn may be, for example, 1000 g/mol to 1 000 000 g/mol.

In particular, the polymers according to the invention have a molar mass distribution (molecular weight distribution) with a number average $M_n$ from 1000 to 200 000 g/mol, preferably from 2000 to 180 000 g/mol, particularly preferably from 3000 to 150 000 g/mol, particularly from 5000 bis 100 000 g/mol and, by way of example, 10 000 g/mol to 50 000 g/mol.

The invention further provides methods for preparing polymers.

The preparation may be carried out in particular by means of free-radical polymerization of unsaturated compounds of the general formula (I), preferably (Ia), particularly preferably (Ib) and also optionally further monomers. Methods for free-radical polymerization of monomers are known in principle to those skilled in the art.

The free-radical polymerization can be carried out in bulk or preferably in solution. In the polymerization in solution, the choice of solvent is determined by the type of unsaturated compounds (I) and also optionally further monomers, particularly by the hydrophilicity of the monomers. The polymerization can be carried out in polar solvents in particular, preferably in aqueous solution. Preference is given to using aqueous solutions in which the solvent or solvent mixture used comprises at least 50% by weight water. In addition, further water-miscible solvents may be present, e.g. alcohols. An aqueous solvent preferably comprises at least 70% by weight water, particularly preferably at least 90% by weight water. For example, the method can be carried out exclusively in water.

To start the polymerization, initiators for the free-radical polymerization known in principle are used and in this case can in particular take the form of thermal polymerization initiators, for example, peroxides or azo initiators. The polymerization temperature is selected by those skilled in the art depending on the desired result. A temperature of 50° C. to 100° C. has been found to be useful, particularly in the polymerization in aqueous solution. The free-radical polymerization can also be carried out by means of other techniques; it can take the form of a photopolymerization using photoinitiators for example.

The pH during the course of the polymerization in aqueous solution may be selected by those skilled in the art depending on the desired result. The compounds (I) according to the invention are also stable to hydrolysis in the acidic range. This differs from the analogous vinyl ether compounds $H_2C=CH-O-R-(AO)_x$ known from the prior art, which tend to hydrolysis in the acidic range, particularly at pH values below 3. This significantly reduces their potential uses. The compounds (I) according to the invention, optionally together with further monomers, may be particularly advantageously free-radically polymerized in aqueous solution in the acidic pH range, particularly at pH 1 to 6, preferably 1 to 5 and particularly pH 1 to 3.

The free-radical polymerization may be carried out, for example, in a batch process, semi-batch process or by means of a continuous process. A suitable continuous process is described, for example, in WO 2009/100956 A2.

Various techniques can be used in the free-radical polymerization of unsaturated compounds (I), preferably compounds (Ia), particularly preferably compounds (Ib), with further monomers, particularly with further monomers comprising acid groups, for example, acrylic acid in aqueous solution. In one embodiment of the invention, a mixture of the monomers as such or in solution is initially charged in a reaction vessel and the polymerization is then started, for example by adding a thermal polymerization initiator and raising the temperature.

In a further embodiment of the invention, a solution of the unsaturated compounds (I) and also optionally a portion of the further monomers and a portion of a thermal polymerization initiator is initially charged in the reaction vessel. In this embodiment, not more than 25% by weight of the further monomers should be initially charged. The remaining amount of the further monomers and also the remaining amount of the initiator are added after the start of the polymerization, in particular after heating to the polymerization temperature. In this case, a solution of further monomers and a solution of the initiator are preferably metered in continuously into the reaction vessel.

In a preferred embodiment of the invention, the unsaturated compounds (I) and the further monomers are metered in gradually into the polymerization reactor, which contains at least a certain amount of solvent, in particular an aqueous solvent.

In this embodiment, only a portion of the unsaturated compounds (I), of the further monomers and also of the initiator are initially charged in the reaction vessel, wherein the amount of monomers initially charged should not exceed 25% by weight of the total amount, preferably 10% by weight of the intended total amount of the monomers, and where furthermore the molar ratio of the monomers initially charged should be selected to correspond to the ratio intended in the polymer. The deviation should generally not be more than +/−20%, preferably not more than +/−10% of the intended ratio. The ratio of monomers initially charged particularly preferably corresponds to the desired monomer ratio.

The polymerization of the portions of the monomers initially charged is initially started. This can be effected by heating the batch to the desired polymerization temperature. Alternatively, an initiator can be added which starts the polymerization already at room temperature, e.g. a redox initiator. The polymerization then starts when the initiator is added to the monomers. After the start, the unsaturated compounds (I) and the further monomers are added, preferably as solutions. In this case, the monomers can be added separately, or a mixture of unsaturated compounds (I) and further monomers can also be added, preferably a solution of unsaturated compounds (I) and further monomers in a suitable solvent. In the latter case, the ratio of the unsaturated compounds (I) to the further monomers is naturally fixed, whereas in the first case the ratio may also be varied during the polymerization. The initiator is likewise metered in as a solution in a suitable solvent.

The rate of addition during the addition of the unsaturated compounds (I) and the further monomers should be selected here in each case such that too large an excess of unpolymerized unsaturated compounds (I) or unpolymerized further monomers in the reaction vessel is avoided. An excess of unpolymerized unsaturated compounds (I) should be particularly avoided. The molar ratio of unsaturated compounds (I)/further monomers will be referred to below as x. The rate of addition of the monomers should preferably be selected such that the molar ratio of the monomers feeding into the reactor does not deviate from the intended ratio by more than +/−20%, preferably not more than +/−10%, wherein evidently the total amount of the monomers must correspond to the desired value.

The embodiment of the polymerization described leads to copolymers having particularly good performance properties. The advantages are particularly significant in the copolymerization of unsaturated compounds (I) with further monomers having further acid groups in aqueous solution, such as acrylic acid. This is further specified in more detail in the examples section. Although we do not wish to be committed to a particular theory, it seems that the effect is due to the fact that the monomers are incorporated particularly uniformly in the preferred embodiment.

The invention further provides methods for preparing polymers, wherein
a. a free-radical polymerization of monomers comprising unsaturated compounds of the general formula (II) and

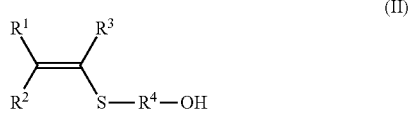

(II)

b. a polymer-analogous reaction of polymers formed in step a. with compounds of the general formula (III)

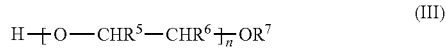

(III)

is carried out, where the symbols and indices have the meanings stated above.

The present invention further relates to the use of polymers according to the invention as cement additives, grinding aids in the production of cement, additives to hydraulic binders, concrete plasticizers, reactive plasticizers for preparing plastics (such as polyvinyl alcohol, polyvinyl butyraldehyde), rubber or latex (such as styrene/butadiene rubber—SBR, nitrile/butadiene rubber—NBR), associative thickeners, antioxidants, or for preparing polyether siloxanes.

The present invention further relates to mixtures comprising polymers according to the invention.

The polymers according to the invention are preferably used as concrete plasticizers, preferably in mixtures which serve to plasticize concrete. Such mixtures generally comprise a flow agent of the polycarboxylate ether type, optionally in combination with a concrete plasticizer of the lignin sulfonate type and/or beta-naphthalene sulfonic acid-formaldehyde co-condensate, deaerator, air-entraining additive, accelerator or retarder and also water.

Particularly suitable for use as concrete plasticizers are copolymers comprising unsaturated compounds (I) and also at least one further monomer, in particular at least one monoethylenically unsaturated further monomer. The unsaturated compounds (I) for this application are preferably compounds (Ia), particularly preferably compounds (Ib), where n in formula (Ib) is preferably from 20 to 140, particularly from 20 to 60 and especially preferably from 20 to 30. Examples of particularly suitable further monomers for use as concrete plasticizers include acrylic acid, methacrylic acid, maleic anhydride, hydroxyethyl (meth)acrylate, hydroxypropyl (meth)acrylate, hydroxyethyl (meth)acrylate phosphate, hydroxypropyl (meth)acrylate phosphate.

Suitable copolymers for use as concrete plasticizers generally comprise 55 to 99.9% by weight unsaturated compounds (I) and 0.1 to 45% by weight monoethylenically unsaturated further monomer, wherein the total amount of unsaturated compounds (I) and of monoethylenically unsaturated further monomers, particularly those just mentioned, is at least 90% by weight, particularly preferably at least 95% by weight. With very particular preference, no other monomers are present besides compounds of the formula (I) and monoethylenically unsaturated further monomers. For this application, the number-average molecular weight $M_n$ is preferably 1000 g/mol to 100 000 g/mol, particularly 5000 g/mol to 100 000 g/mol and, by way of example, 10 000 g/mol to 40 000 g/mol.

Further preferred mixtures are mixtures of the polymers according to the invention with other polymers, preferably elastomers. Examples of such polymers are rubber, polyvinyl alcohol, polyvinyl butyral, polyvinyl chloride, polyvinyl butyraldehyde.

If rubbers are selected as polymers, such rubbers preferably comprise rubber types selected from the groups consisting of SBR rubber, for example S-SBR rubber or E-SBR rubber, BR rubber, EPM rubber, EPDM rubber, SB rubber, IIR rubber, NBR rubber and CR rubber, preferably SBR rubber, NBR rubber.

The present invention provides reactive alkoxylate monomers stable to hydrolysis which can be efficiently converted to polymers stable to hydrolysis.

The invention is illustrated in detail by the examples without the examples restricting the subject matter of the invention.

EXAMPLES

VME: vinylmercaptoethanol $H_2C=CH-S-CH_2CH_2OH$
HBVE: hydroxybutyl vinyl ether $H_2C=CH-O-CH_2CH_2CH_2CH_2OH$ Methods of Measurement:
OH Number:

The OH number (OHN) is a measure of the alcohol groups present in a sample. The determination is carried out by esterifying the alcohol groups with an excess of acetic anhydride. Following hydrolysis of the unreacted acetic anhydride, the residual free acetic acid is titrated with KOH. The OH number data are expressed in units of mg KOH/g of sample. The OH number therefore corresponds to the amount of KOH in "mg", which is equivalent to the amount of acetic acid linked to the acetylation of 1 g of substance.

PEG Content:

The polyethylene glycol content is defined as the proportion of PEG in nonionic surfactants and EO adducts which may be determined by thin-layer chromatography. This is stated as g per 100 grams. Polyethylene glycol is separated from oxyethylate in a substance spot by thin-layer chromatography using a ready-to-use HPTLC plate and is quantified by remission location curve measurement after derivatization with Dragendorff's reagent. The evaluation is conducted after calibration with a PEG standard (PEG 1000).

GPC Measurement
(For all Experiments Except 5a to 5 g and Comparative Experiments 5a to 5c):
Columns:

The following columns from PSS Mainz were connected in series:

PSS Suprema pre-column
PSS Suprema 30 Å, 10μ 8×300 mm
PSS Suprema 1000 Å, 10μ 8×300 mm
PSS Suprema 3000 Å, 10μ 8×300 mm
and maintained at 35° C.
Column Material:
Modified acrylate copolymer network.
Eluent:
Phosphate buffer pH 9.7
0.0239 mol/L disodium hydrogen phosphate (dihydrate),
pH 9.7, adjusted with NaOH 2 mol/L,
0.5 g/L sodium azide.
The samples are diluted with the eluent.
Instruments/Software:
Agilent 1100 system with ChemStation, evaluation using PSS WinGPC Unity.
Conditions:
Sample Dilution:
1.5 mL eluent+10 μL acetone (internal standard)+20 μL sample (up to max. 50% solution, less at higher concentration),
Injection: 50 μL, with needle wash,
Flow rate: 0.8 mL/min,
Run time: 60 min,
Detector: RID (Agilent G1362A), 35° C.
Calibration:
Calibration standards from PSS: Polyethylene glycol (PEG), polyethylene oxide (PEO) for high molar masses. Internal standard for compensation of flow rate variations: acetone.
GPC Methods for Experiments 5a to 5 g and Comparative Experiments 5a to 5c (See Table 4):
column combinations: OHpak SB-G, OHpeak SB 804 HQ and OHpak SB 802.5 HQ from Shodex, Japan; eluent: 80% by volume aqueous solution of $HCO_2NH_4$ (0.05 mol/l) and 20% by volume acetonitrile; injection volume 100 μl; flow rate 0.5 ml/min). The calibration in order to determine the average molar mass took place using linear polyethylene glycol standards. The polymer peak is normalized to a relative height of 1 as a measure of the conversion and the peak height of the unreacted macromonomer/PEG-containing oligomer is used as a measure of the residual monomer content.

Example 1

Preparation of Alkoxylates of S-vinylthioalkanols

Example 1a

Reaction scheme:

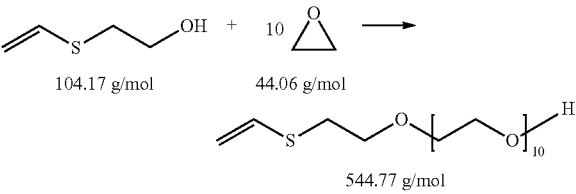

A 2 L autoclave was charged with 104 g (1.00 mol) of vinylmercaptoethanol and 2.18 g (19.4 mmol KOH) of an aqueous potassium hydroxide solution (50% by weight) at 70° C. and the water was removed at <20 mbar over a period of 2 h. The autoclave was then flushed with nitrogen and the temperature increased to 130° C. 440 g (10.0 mol) of ethylene oxide were added over a period of 4 h. The reaction mixture obtained was then stirred for 10 h at 130° C. and, after cooling to 100° C., was freed from volatile constituents under reduced pressure.

572 g of a brown liquid were obtained.

OHN=102.5 mg KOH/g (theory 103.0 mg KOH/g)

Example 1b

Reaction scheme:

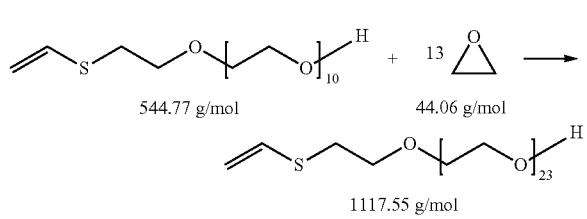

A 2 L autoclave was charged with 164 g (0.30 mol) of vinylmercaptoethanol*10EO (example 1a) and 686 mg (6.11 mmol KOH) of an aqueous potassium hydroxide solution (50% by weight) at 100° C. and the water was removed at <20 mbar over a period of 2 h. The autoclave was then flushed with nitrogen and the temperature increased to 130° C. 172 g (3.90 mol) of ethylene oxide were added over a period of 1.5 h. The reaction mixture obtained was then stirred for 8 h at 130° C. and, after cooling to 100° C., was freed from volatile constituents under reduced pressure.

337 g of a brown solid were obtained.

OHN=55.6 mg KOH/g (theory 50.2 mg KOH/g); PEG content=10.5% by weight.

Example 1c

Reaction scheme:

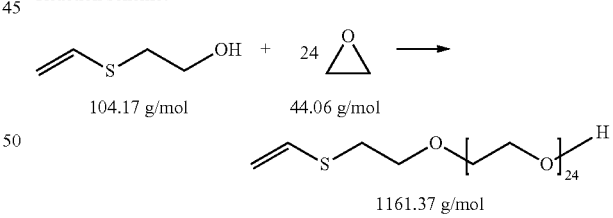

A 2 L autoclave was charged with 52.1 g (0.50 mol) of vinylmercaptoethanol and 410 mg (1.87 mmol KOMe) of a methanolic potassium methoxide solution (32% by weight in methanol) at 65° C. and the methanol was removed at <20 mbar over a period of 2 h. The autoclave was then flushed with nitrogen and the temperature increased to 120° C. 528 g (12.0 mol) of ethylene oxide were added over a period of 4 h. The reaction mixture obtained was then stirred for 10 h at 120° C. and, after cooling to 100° C., was freed from volatile constituents under reduced pressure.

606 g of a brown solid were obtained.

OHN=47.5 mg KOH/g (theory 48.8 mg KOH/g), PEG content: <1% by weight

Example 1d

Reaction scheme:

[Structure: vinyl-S-CH2CH2-OH (104.17 g/mol) + 24 ethylene oxide (44.06 g/mol) → vinyl-S-CH2CH2-O-(CH2CH2O)24-H (1161.37 g/mol)]

A 2 L autoclave was charged with 104 g (1.00 mol) of vinylmercaptoethanol and 289 mg (90%, 4.50 mmol KOH) of KOH flakes in 416 g of toluene at 60° C. and flushed with nitrogen. The temperature was then increased to 120° C. 1057 g (24.0 mol) of ethylene oxide were added over a period of 13 h. The reaction mixture obtained was then stirred for 10 h at 120° C. and, after cooling to 105° C., was freed from volatile constituents under reduced pressure.

1181 g of a light brown solid were obtained.

OHN=50.6 mg KOH/g (theory 48.8 mg KOH/g), PEG content: <1% by weight

Example 1e

Reaction scheme:

[Structure: vinyl-S-CH2CH2-OH + 10 propylene oxide → vinyl-S-CH2CH2-O-(CH(CH3)CH2O)10-H]

A 2 L autoclave was charged with 104 g (1.00 mol) of vinylmercaptoethanol and 641 mg (2.97 mmol KOMe) of a methanolic potassium methoxide solution (32% by weight in methanol) at 60° C. and the methanol was removed at <20 mbar over a period of 2 h. The autoclave was then flushed with nitrogen and the temperature increased to 130° C. 581 g (10.0 mol) of propylene oxide were added over a period of 10 h. The reaction mixture obtained was then stirred for 10 h at 130° C. and, after cooling to 100° C., was freed from volatile constituents under reduced pressure.

629 g of a dark brown solid were obtained.

OHN=88.0 mg KOH/g (theory 81.9 mg KOH/g)

Example 1f

Reaction scheme:

[Structure: vinyl-S-CH2CH2-O-(CH(CH3)CH2O)10-H + 33 ethylene oxide → vinyl-S-CH2CH2-O-(CH(CH3)CH2O)10-(CH2CH2O)33-H]

A 2 L autoclave was charged with 188 g (275 mmol) of vinylmercaptoethanol*10PO (example 1e) and 1.85 g (16.6 mmol KOH) of an aqueous potassium hydroxide solution (50% by weight) at 100° C. and the water was removed at <20 mbar over a period of 2 h. The autoclave was then flushed with nitrogen and the temperature increased to 120° C. 396 g (9.00 mol) of ethylene oxide were added over a period of 6 h. The reaction mixture obtained was then stirred for 5 h at 120° C. and, after cooling to 90° C., was freed from volatile constituents under reduced pressure.

597 g of a light brown solid were obtained.

OHN=31.8 mg KOH/g (theory 28.8)

Example 1g

Reaction scheme:

[Structure: vinyl-S-CH2CH2-O-(CH(CH3)CH2O)10-H + 125 ethylene oxide → vinyl-S-CH2CH2-O-(CH(CH3)CH2O)10-(CH2CH2O)125-H]

A 2 L autoclave was charged with 68.4 g (0.10 mmol) of vinylmercaptoethanol*10PO (example 1e) and 0.62 g (5.52 mmol KOH) of an aqueous potassium hydroxide solution (50% by weight) at 100° C. and the water was removed at <20 mbar over a period of 2 h. The autoclave was then flushed with nitrogen and the temperature increased to 120° C. 550 g (12.5 mol) of ethylene oxide were added over a period of 6 h. The reaction mixture obtained was then stirred for 5 h at 120° C. and, after cooling to 90° C., was freed from volatile constituents under reduced pressure.

610 g of a brown solid were obtained.

OHN=12.2 mg KOH/g (theory 9.2), PEG content: 1.4% by weight

Example 1h

Reaction scheme:

[Structure: vinyl-S-CH2CH2-OH (104.17 g/mol) + 67 ethylene oxide (44.06 g/mol) → vinyl-S-CH2CH2-O-(CH2CH2O)67-H (3065.52 g/mol)]

A 2 L autoclave was charged with 46.7 g (448 mmol) of vinylmercaptoethanol and 120 mg (1.71 mmol) of potassium methoxide in 100 mL of toluene at 60° C. and flushed with nitrogen. The temperature was then increased to 120° C. 1321 g (30.0 mol) of ethylene oxide were added over a period of 20 h. The reaction mixture obtained was then stirred for 10 h at 120° C. and, after cooling to 100° C., was freed from volatile constituents under reduced pressure.

1396 g of a light brown solid were obtained.

OHN=21.2 mg KOH/g (theory 18.4 mg KOH/g), PEG content: 1.4% by weight

Example 1i

Reaction scheme:

$$\text{CH}_2=\text{CH}-\text{S}-\text{CH}_2\text{CH}_2-\text{OH} + 135 \underset{\triangle}{\text{O}} \longrightarrow$$

104.17 g/mol    44.06 g/mol $$\text{CH}_2=\text{CH}-\text{S}-\text{CH}_2\text{CH}_2-\text{O}-[\text{CH}_2\text{CH}_2\text{O}]_{135}-\text{H}$$

6050.92 g/mol

A 2 L autoclave was charged with 23.4 g (224 mmol) of vinylmercaptoethanol and 120 mg (1.71 mmol) of potassium methoxide in 50 mL of toluene at 60° C. and flushed with nitrogen. The temperature was then increased to 120° C. 1332 g (30.2 mol) of ethylene oxide were added over a period of 36 h. The reaction mixture obtained was then stirred for 12 h at 120° C. and, after cooling to 100° C., was freed from volatile constituents under reduced pressure.

1388 g of a light brown solid were obtained.

OHN=12.1 mg KOH/g (theory 9.3 mg KOH/g), PEG content: 2.0% by weight

Comparative Example 1j

Preparation of HBVE-24 EO

The procedure was as in Example 1c, only a corresponding amount of HBVE was used in place of VME.

Comparative Example 1k

Preparation of HBVE-67 EO

The procedure was as in Example 1 h, only a corresponding amount of HBVE was used in place of VME.

Comparative Example 1l

Preparation of HBVE-135 EO

The procedure was as in Example 1i, only a corresponding amount of HBVE was used in place of VME.

Example 2

Preparation of Polymers, Method (A)

In method (A), the VME or HBVE alkoxylates are initially charged for the polymerization

Example 2a

Copolymer of 89% by weight VME-23EO and 11% by weight acrylic acid
Polymerization at pH 2-3 (azo starter)

35.6 g of VME ethoxylate (23EO) according to Example 1 b were dissolved in 63.5 g of water in a glass reactor equipped with stirrer, reflux condenser, thermometer, nitrogen line and addition lines. A portion (1.1 g) of a solution A (4.4 g of acrylic acid dissolved in 18.4 g of water) and a portion (2 g) of a solution B (1.6 g of 2,2'-azobis[2-(2-imidazolin-2-yl)propane]dihydrochloride (Wako VA-44) dissolved in 38.1 g of water) were added. The polymerization was started by heating the solution under nitrogen to 70° C. and the remaining amounts of solutions A and B were then added, wherein solution A was added over 3 hours and solution B over 4 hours. The reaction mixture was then stirred at 70° C. for 2 h.

Data relating to the synthesis and also $M_n$, $M_w$ and PDI of the resulting polymer are summarized in Table 1.

Example 2b

The procedure was as in Example 2a, only the amount of initiator was reduced from 1.6 g to 1.2 g. Data relating to the synthesis and also $M_n$, $M_w$ and PDI of the resulting polymer are summarized in Table 1.

Example 2c

The procedure was as in Example 2a, only the amount of initiator was reduced from 1.6 g to 0.8 g. Data relating to the synthesis and also $M_n$, $M_w$ and PDI of the resulting polymer are summarized in Table 1.

Comparative Example 2a

Copolymer of 89% by weight HBVE-24EO and 11% by weight acrylic acid 35.6 g of HBVE-24EO according to comparative example 1i were dissolved in 63.5 g of water in a glass reactor equipped with stirrer, reflux condenser, thermometer, nitrogen line and addition lines. A portion (1.1 g) of a solution A (4.4 g of acrylic acid dissolved in 18.4 g of water) and a portion (2 g) of a solution B (1.6 g of 2,2'-azobis[2-(2-imidazolin-2-yl)propane]dihydrochloride (Wako VA-44) dissolved in 38.1 g of water) were added. The polymerization was started by heating the solution under nitrogen to 70° C. and the remaining amounts of solutions A and B were then added, wherein solution A was added over 3 hours and solution B over 4 hours. The reaction mixture was then stirred at 70° C. for 2 h.

Data relating to the synthesis and also $M_n$, $M_w$ and PDI of the resulting polymer are summarized in Table 1.

Comparative Example 2b

The procedure was as in Example 2, only the amount of initiator was reduced from 1.6 g to 1.2 g. Data relating to the synthesis and also $M_n$, $M_w$ and PDI of the resulting polymer are summarized in Table 1.

Comparative Example 2c

The procedure was as in Example 2, only the amount of initiator was reduced from 1.6 g to 0.8 g. Data relating to the synthesis and also $M_n$, $M_w$ and PDI of the resulting polymer are summarized in Table 1.

A GPC measurement of the reaction products from example 2a and comparative example 2a showed an additional strongly pronounced low molecular weight peak in the case of HBVE-24EO (comparative example 2a). In the case of the HBVE ethoxylates, a large proportion of the monomers was hydrolyzed during the polymerization.

Furthermore, in 1H-NMR measurements of comparative examples 2a, 2b and 2c, vinyl compound was no longer observed.

Example 2d

Copolymer of 85% by weight VME-23EO and 15% by weight Na acrylate
Polymerization at pH 7-8 (azo starter)

34.0 g of VME ethoxylate-23EO according to Example 1b were dissolved in 63.5 g of water in a glass reactor equipped with stirrer, reflux condenser, thermometer, nitrogen line and addition lines. A portion (1.2 g) of a solution A (6.0 g of acrylic acid Na salt dissolved in 18.4 g of water) and a portion (2 g) of a solution B (1.6 g of 2,2'-azobis[2-(2-imidazolin-2-yl)propane]dihydrochloride (Wako VA-44) dissolved in 38.1 g of water) were added. The polymerization was started by heating the solution under nitrogen to 70° C. and the remaining amounts of solutions A and B were then added, wherein solution A was added over 3 hours and solution B over 4 hours. The reaction mixture is then stirred at 70° C. for 2 h.

Data relating to the synthesis and also $M_n$, $M_w$ and PDI of the resulting polymer are summarized in Table 1.

Comparative Example 2d

Copolymer of 85% by weight HBVE-24EO and 15% by weight Na acrylate
Polymerization at pH 7-8 (azo starter)

34.0 g of HBVE-24EO according to example 1i were dissolved in 63.5 g of water in a glass reactor equipped with stirrer, reflux condenser, thermometer, nitrogen line and addition lines. A portion (1.2 g) of a solution A (6.0 g of acrylic acid sodium salt dissolved in 18.4 g of water) and a portion (2 g) of a solution B (1.6 g of 2,2'-azobis[2-(2-imidazolin-2-yl)propane]dihydrochloride (Wako VA-44) dissolved in 38.1 g of water) were added. The polymerization was started by heating the solution under nitrogen to 70° C. and the remaining amounts of solutions A and B were then added, wherein solution A was added over 3 hours and solution B over 4 hours. The reaction mixture was then stirred at 70° C. for 2 h.

No hydrolysis of HBVE ethoxylate was observed at neutral pH. $^1$H-NMR measurement of the polymer revealed that ca. 8% of the HBVE ethoxylate used had not been polymerized. The molar mass of the HBVE ethoxylate/acrylic acid copolymer was distinctly lower than that of the VME ethoxylate-acrylic acid copolymer.

Data relating to the synthesis and also $M_n$, $M_w$ and PDI of the resulting polymer are summarized in Table 1.

Example 2e

Copolymer of 89% by weight VME-23EO and 11% by weight acrylic acid
Polymerization at pH 1.9 (peroxide starter)

42.7 g of VME ethoxylate-24EO according to example 1d were dissolved in 38.8 g of water in a glass reactor equipped with stirrer, reflux condenser, thermometer, nitrogen line and addition lines. The solution was heated under nitrogen to 95° C. and addition of solutions A (5.3 g of acrylic acid dissolved in 41.4 g of water) and B (1.9 g of sodium peroxodisulfate dissolved in 31.4 g of water) initiated, wherein solution A was added over 4 hours and solution B over 5 hours. The reaction mixture was then stirred at 95° C. for 2 h.

Data relating to the synthesis and also $M_n$, $M_w$ and PDI of the resulting polymer are summarized in Table 1.

Comparative Example 2e

Copolymer of 89% by weight HBVE-24EO and 11% by weight acrylic acid
Polymerization at pH 1.9

42.7 g of HBVE-24EO according to comparative example 1j were dissolved in 38.8 g of water in a glass reactor equipped with stirrer, reflux condenser, thermometer, nitrogen line and addition lines. The solution was heated under nitrogen to 95° C. and addition of solutions A (5.3 g of acrylic acid dissolved in 41.4 g of water) and B (1.9 g of sodium peroxodisulfate dissolved in 31.4 g of water) initiated, wherein solution A was added over 4 hours and solution B over 5 hours. The reaction mixture was then stirred at 95° C. for 2 h.

An intense hydrolysis of HBVE ethoxylate was observed. A large peak at low molar masses was observed in the GPC.

Data relating to the synthesis and also $M_n$, $M_w$ and PDI of the resulting polymer are summarized in Table 1.

Example 2f

Polymerization in Bulk

Copolymer of 89% by weight VME-24EO and 11% by weight acrylic acid 71.2 g of VME-24EO according to example 1d and 2.4 g of 2-mercaptoethanol were initially charged in a glass reactor equipped with stirrer, reflux condenser, thermometer, nitrogen line and addition lines. The mixture was heated under nitrogen to 85° C. and addition of 8.7 g of acrylic acid and 3.2 g of tert-butyl peroctoate initiated, wherein the acrylic acid was added over 3 hours and initiator over 4 hours. The reaction mixture was then stirred at 85° C. for 4 h.

Data relating to the synthesis and also $M_n$, $M_w$ and PDI of the resulting polymer are summarized in Table 1.

Comparative Example 2f

Copolymer of 89% by weight HBVE-24EO and 11% by weight acrylic acid 71.2 g of HBVE-24EO according to comparative example 1j and 2.4 g of 2-mercaptoethanol were initially charged in a glass reactor equipped with stirrer, reflux condenser, thermometer, nitrogen line and addition lines. The mixture was heated under nitrogen to 85° C. and addition of 8.7 g of acrylic acid and 3.2 g of tert-butyl peroctoate initiated, wherein the acrylic acid was added over 3 hours and initiator over 4 hours. The reaction mixture was then stirred at 85° C. for 4 h.

Data relating to the synthesis and also $M_n$, $M_w$ and PDI of the resulting polymer are summarized in Table 1.

Polymers according to the invention can also be prepared in bulk (without solvent). For polymerization in bulk, the monomers are treated with an azo starter. For example, the copolymerization of VME ethoxylate and acrylic acid in bulk is also possible using peroctoate as initiator at 85° C. Regulators can also be used in the polymerization in bulk, for example, mercaptoethanol or mercaptopropionic acid.

Example 2g

Polymerization of Long-chain VME Ethoxylates

Copolymer of 81% by weight VME-67EO and 19% by weight acrylic acid
Polymerization at pH 2-3 (azo starter)

32.6 g of VME ethoxylate (67EO) according to Example 1h were dissolved in 63.5 g of water in a glass reactor equipped with stirrer, reflux condenser, thermometer, nitrogen line and addition lines. A portion (1.3 g) of a solution A (7.6 g of acrylic acid dissolved in 18.4 g of water) and a portion (2 g) of a solution B (1.6 g of 2,2'-azobis[2-(2-imidazolin-2-yl)propane]dihydrochloride (Wako VA-44) dissolved in 38.1 g of water) were added. The polymerization was started by heating the solution under nitrogen to 70° C. and the remaining amounts of solutions A and B were then added, wherein solution A was added over 3 hours and solution B over 4 hours. The reaction mixture was then stirred at 70° C. for 2 h.

Data relating to the synthesis and also $M_n$, $M_w$ and PDI of the resulting polymer are summarized in Table 1.

Comparative Example 2g

Copolymer of 81% by weight HBVE-67EO and 19% by weight acrylic acid
Polymerization at pH 2-3 (azo starter)

32.4 g of HBVE ethoxylate (67EO) according to comparative example 1k were dissolved in 57.6 g of water in a glass reactor equipped with stirrer, reflux condenser, thermometer, nitrogen line and addition lines. A portion (1.6 g) of a solution A (7.6 g of acrylic acid dissolved in 24.0 g of water) and a portion (2 g) of a solution B (1.6 g of 2,2'-azobis[2-(2-imidazolin-2-yl)propane]dihydrochloride (Wako VA-44) dissolved in 38.4 g of water) were added. The polymerization was started by heating the solution under nitrogen to 70° C. and the remaining amounts of solutions A and B were then added, wherein solution A was added over 3 hours and solution B over 4 hours. The reaction mixture was then stirred at 70° C. for 2 h.

Data relating to the synthesis and also $M_n$, $M_w$ and PDI of the resulting polymer are summarized in Table 1.

A GPC measurement of the reaction products from example 2g and comparative example 2g showed an additional strongly pronounced low molecular weight peak in the case of HBVE-24EO (comparative example 2g). In the case of the HBVE ethoxylates, a large proportion of the monomers was hydrolyzed during the polymerization. Furthermore, in 1H-NMR measurements of comparative examples 2g, vinyl compound was again observed.

Example 2h

Copolymer of 81% by weight VME-135EO and 19% by weight acrylic acid
Polymerization at pH 2-3 (azo starter)

32.3 g of VME ethoxylate (135EO) were dissolved in 63.5 g of water in a glass reactor equipped with stirrer, reflux condenser, thermometer, nitrogen line and addition lines. A portion (1.3 g) of a solution A (7.7 g of acrylic acid dissolved in 18.4 g of water) and a portion (2 g) of a solution B (1.6 g of 2,2'-azobis[2-(2-imidazolin-2-yl)propane]dihydrochloride (Wako VA-44) dissolved in 38.2 g of water) were added. The polymerization was started by heating the solution under nitrogen to 70° C. and the remaining amounts of solutions A and B were then added, wherein solution A was added over 3 hours and solution B over 4 hours. The reaction mixture was then stirred at 70° C. for 2 h.

Data relating to the synthesis and also $M_n$, $M_w$ and PDI of the resulting polymer are summarized in Table 1.

Comparative Example 2h

Copolymer of 81% by weight HBVE-135EO and 19% by weight acrylic acid
Polymerization at pH 2-3 (azo starter)

32.3 g of HBVE ethoxylate (135EO) according to comparative example 11 were dissolved in 57.6 g of water in a glass reactor equipped with stirrer, reflux condenser, thermometer, nitrogen line and addition lines. A portion (1.6 g) of a solution A (7.7 g of acrylic acid dissolved in 24.0 g of water) and a portion (2 g) of a solution B (1.6 g of 2,2'-azobis[2-(2-imidazolin-2-yl)propane]dihydrochloride (Wako VA-44) dissolved in 38.4 g of water) were added. The polymerization was started by heating the solution under nitrogen to 70° C. and the remaining amounts of solutions A and B were then added, wherein solution A was added over 3 hours and solution B over 4 hours. The reaction mixture was then stirred at 70° C. for 2 h.

Data relating to the synthesis and also $M_n$, $M_w$ and PDI of the resulting polymer are summarized in Table 1.

TABLE 1

Results of the polymer syntheses (*amount of residual monomer by NMR, AA = acrylic acid, amounts in % by weight)

| | | Initiator | | pH during | $M_n$ | $M_w$ | | Amount of residual monomer |
|---|---|---|---|---|---|---|---|---|
| Experiment | Monomers | Type | Amount | Polymerization | [g/mol] | (g/mol) | $M_w/M_n$ | [mol %] |
| Example 2a | 89% VME-23EO, 11% AA | Azo | 1.6 g | 2.4 | 6348 | 34566 | 5.44 | |
| Example 2b | 89% VME-23EO, 11% AA | Azo | 1.2 g | 2.3 | 6137 | 41648 | 6.78 | |
| Example 2c | 89% VME-23EO, 11% AA | Azo | 0.8 g | 2.4 | 6591 | 42874 | 6.50 | |
| Comparative example 2a | 89% HBVE-24EO, 11% AA | Azo | 1.6 g | 2.4 | 1267 | 12459 | 9.83 | |
| Comparative example 2b | 89% HBVE-24EO, 11% AA | Azo | 1.2 g | 2.4 | 1141 | 4366 | 3.82 | |
| Comparative example 2c | 89% HBVE-24EO, 11% AA | Azo | 0.8 g | 2.5 | 1478 | 17994 | 12.20 | |
| Example 2d | 85% VME-23EO, 11% AA | Azo | 1.6 g | 8.1 | 4974 | 20834 | 4.18 | 0.0 |
| Comparative example 2d | 85% HBVE-24EO, 11% AA | Azo | 1.6 g | 7.8 | 1928 | 9555 | 4.95 | 8.2 |
| Example 2e | 89% VME-24EO, 11% AA | Peroxide | 1.9 g | 1.9 | 2629 | 7008 | 2.66 | |
| Comparative example 2e | 89% HBVE-24 EO, 11% AA | Peroxide | 1.9 g | 1.9 | 864 | 2701 | 3.12 | |
| Example 2f | 89% VME-24EO, 11% AA | Peroxide | 3.2 g | — | 14637 | 139210 | 9.51 | n.d. |
| Comparative example 2f | 89% HBVE-24EO, 11% AA | Peroxide | 3.2 g | — | 7727 | 13592 | 1.75 | n.d. |

TABLE 1-continued

Results of the polymer syntheses (*amount of residual monomer by NMR, AA = acrylic acid, amounts in % by weight)

| Experiment | Monomers | Initiator Type | Initiator Amount | pH during Polymerization | $M_n$ [g/mol] | $M_w$ (g/mol) | $M_w/M_n$ | Amount of residual monomer [mol %] |
|---|---|---|---|---|---|---|---|---|
| Example 2g | 81% VME-67EO, 19% AA | Azo | 1.6 g | 2.5 | 28707 | 140920 | 4.90 | |
| Comparative example 2g | 81% HBVE-67 EO, 19% AA | Azo | 1.6 g | 2.4 | 8605 | 37977 | 4.41 | |
| Example 2h | 81% VME-135EO, 19% AA | Azo | 1.6 g | 2.5 | 23495 | 159210 | 6.78 | |
| Comparative example 2h | 81% HBVE-135 EO, 19% AA | Azo | 1.6 g | 2.4 | 14976 | 56306 | 3.76 | |

Example 3

Preparation of Polymers, Method (B)

In method (B), the VME or HBVE alkoxylates are not initially charged for the polymerization but added gradually during the polymerization.

Example 3a

Copolymer of 89% by weight VME-23EO and 11% by weight acrylic acid (molar ratio 1:2)
Polymerization at pH 2.8 (peroxide starter)

66 g of water, a portion (2.9 g) of solution A (35.6 g of VME-23EO according to Example 1b and 4.4 g of acrylic acid dissolved in 18 g of water) and a portion (1.9 g) of solution B (0.8 g (75% solution) of tert-butyl perpivalate and 36 g of isopropanol) were initially charged in a glass reactor equipped with stirrer, reflux condenser, thermometer, nitrogen line and addition lines. The initial charge was heated under nitrogen to 75° C. and the polymerization started with addition of the remaining amounts of solutions A and B, wherein solution A was added over 3 hours and solution B over 4 hours. The reaction mixture was then stirred at 75° C. for 2 h. Isopropanol was distilled off.

Data relating to the synthesis and also $M_n$, $M_w$ and PDI of the resulting polymer are summarized in Table 2.

Example 3b

Copolymer of 89% by weight VME-23EO and 11% by weight acrylic acid
Polymerization at pH 2.6 (azo starter)

66 g of water, a portion (2.9 g) of solution A (35.6 g of VME-23EO according to Example Ib, 4.4 g of acrylic acid dissolved in 18 g of water) and a portion (1.9 g) of solution B (1.6 2,2'-azobis[2-(2-imidazolin-2-yl)propane]dihydrochloride (Wako VA-44) and 168 g of water) and 36 g of water) were initially charged in a glass reactor equipped with stirrer, reflux condenser, thermometer, nitrogen line and addition lines. The initial charge was heated under nitrogen to 70° C. and the addition of the remaining amounts of solutions A and B was started, wherein solution A was added over 3 hours and solution B over 4 hours. The reaction mixture was then stirred at 70° C. for 2 h.

Data relating to the synthesis and also $M_n$, $M_w$ and PDI of the resulting polymer are summarized in Table 2.

Comparative Example 3a

Copolymer of 86% by weight HBVE-24EO and 14% by weight Na acrylate
Polymerization at pH 8.5 (peroxide starter)

288.7 g of water, a portion (14 g) of solution A (150.8 g of HBVE-24EO according to comparative example 1i, 80.6 g of 30% acrylic acid Na salt solution and 48.5 g of water) and a portion (6.7 g) of solution B (3.5 g (75% solution) of tert-butyl perpivalate and 131.2 g of isopropanol dissolved) were initially charged in a glass reactor equipped with stirrer, reflux condenser, thermometer, nitrogen line and addition lines. The initial charge was heated under nitrogen to 75° C. and the addition of the remaining amounts of solutions A and B was started, wherein solution A was added over 3 hours and solution B over 4 hours. The reaction mixture was then stirred at 75° C. for 2 h. The reaction mixture was maintained constantly at pH 7.5-8.0. Isopropanol was then distilled off.

Data relating to the synthesis and also $M_n$, $M_w$ and PDI of the resulting polymer are summarized in Table 2.

Comparative Example 3b

Copolymer of 86% by weight HBVE-24EO and 14% by weight Na acrylate
Polymerization at pH 2-3 (azo starter)

252 g of water, a portion (14 g) of solution A (150.8 g of HBVE-24EO according to Example 1i, 80.6 g of 30% acrylic acid Na salt solution and 48.5 g of water) and a portion (8.6 g) of solution B (3.5 g of 2,2'-azobis[2-(2-imidazolin-2-yl)propane]dihydrochloride (Wako VA-44) and 168 g of water) were initially charged in a glass reactor equipped with stirrer, reflux condenser, thermometer, nitrogen line and addition lines. The initial charge was heated under nitrogen to 70° C. and the addition of the remaining amounts of solutions A and B was started, wherein solution A was added over 3 hours and solution B over 4 hours. The reaction mixture was then stirred at 70° C. for 2 h. The reaction mixture was maintained constantly at pH 7.5-8.0.

Data relating to the synthesis and also $M_n$, $M_w$ and PDI of the resulting polymer are summarized in Table 2.

Example 3c

Copolymer of 97% by weight VME-135EO and 3% by weight Na acrylate
Polymerization at pH 9.4 (peroxide starter)

39.4 g of water, a portion (4.4 g) of solution A (36.4 g of VME-135EO according to Example 1 h, 3.7 g of 30% acrylic acid Na salt solution and 48 g of water) and a portion (1.16 g) of solution B (0.75 g (75% solution) of tert-butyl perpivalate and 22 g of isopropanol dissolved) were initially charged in a glass reactor equipped with stirrer, reflux condenser, thermometer, nitrogen line and addition lines. The initial charge was heated under nitrogen to 75° C. and the addition of the remaining amounts of solutions A and B was started, wherein solution A was added over 3 hours and solution B over 4 hours. The reaction mixture was then stirred at 75° C. for 2 h. Isopropanol was distilled off.

Data relating to the synthesis and also $M_n$, $M_w$ and PDI of the resulting polymer are summarized in Table 2.

mixture was then stirred at 75° C. for 2 h. The reaction mixture was maintained constantly at pH 7.5-8.0. Isopropanol was then distilled off.

Data relating to the synthesis and also $M_n$, $M_w$ and PDI of the resulting polymer are summarized in Table 2.

TABLE 2

Results of the polymer syntheses (*amount of residual monomer by NMR, AA = acrylic acid or Na acrylate, amounts in % by weight)

| Experiment | Monomers | Initiator Type | Initiator Amount | pH during Polymerization | $M_n$ [g/mol] | $M_w$ (g/mol) | $M_w/M_n$ | Unreacted ethoxylate monomer [%]* |
|---|---|---|---|---|---|---|---|---|
| Example 3a | 89% VME-23EO, 11% AA | Peroxide | 1.9 g | 2.8 | 27709 | 42697 | 1.54 | 0.0 |
| Comparative example 3a | 86% HBVE-24EO, 14% AA | Peroxide | 3.5 g | 8.7 | 12238 | 15404 | 1.26 | 17 |
| Example 3b | 89% VME-23EO, 11% AA | Azo | 1.9 g | 2.6 | 23197 | 37150 | 1.6 | 0.0 |
| Comparative example 3b | 86% HBVE-24EO, 14% AA | Azo | 8.6 g | 8.5 | 18028 | 25349 | 1.41 | 50 |
| Example 3c | 97% VME-135EO, 3% AA | Peroxide | 0.75 g | 9.4 | 15682 | 20930 | 1.33 | 0.0 |
| Comparative example 3c | 94% HBVE-135EO, 6% AA | Peroxide | 3.5 g | 7.7 | 36819 | 39428 | 1.07 | 37 |
| Example 3d | 97% VME-135EO, 3% AA | Azo | 0.75 g | 8.6 | 18776 | 29705 | 1.58 | 0 |

Example 3d

Copolymer of 97% by weight VME-135EO and 3% by weight Na acrylate
Polymerization at pH 8.6 (azo starter)

45 g of water, a portion (4.4 g) of solution A (36.7 g of VME-135EO according to Example 1 h, 3.7 g of 30% acrylic acid Na salt solution and 48 g of water) and a portion (0.88 g) of solution B (0.75 g of 2,2'-azobis[2-(2-imidazolin-2-yl)propane]dihydrochloride (Wako VA-44) and 17 g of water) were initially charged in a glass reactor equipped with stirrer, reflux condenser, thermometer, nitrogen line and addition lines. The initial charge was heated under nitrogen to 70° C. and the addition of the remaining amounts of solutions A and B was started, wherein solution A was added over 3 hours and solution B over 4 hours. The reaction mixture was then stirred at 70° C. for 2 h.

Data relating to the synthesis and also $M_n$, $M_w$ and PDI of the resulting polymer are summarized in Table 2.

Comparative Example 3c

Copolymer of 94% by weight HBVE-135EO and 6% by weight Na acrylate
Polymerization at pH 7.7 (peroxide starter)

238.7 g of water, a portion (14.0 g) of solution A (164.9 g of HBVE-135EO according to comparative example 1j, 33.7 g of 30% acrylic acid Na salt solution and 131.4 g of water) and a portion (6.7 g) of solution B (3.5 g (75% solution) of tert-butyl perpivalate and 131.2 g of isopropanol dissolved) were initially charged in a glass reactor equipped with stirrer, reflux condenser, thermometer, nitrogen line and addition lines. The initial charge was heated under nitrogen to 75° C. and the addition of the remaining amounts of solutions A and B was started, wherein solution A was added over 3 hours and solution B over 4 hours. The reaction Example 4

Polymerization of VME Ethoxylates with Methacrylic Acid

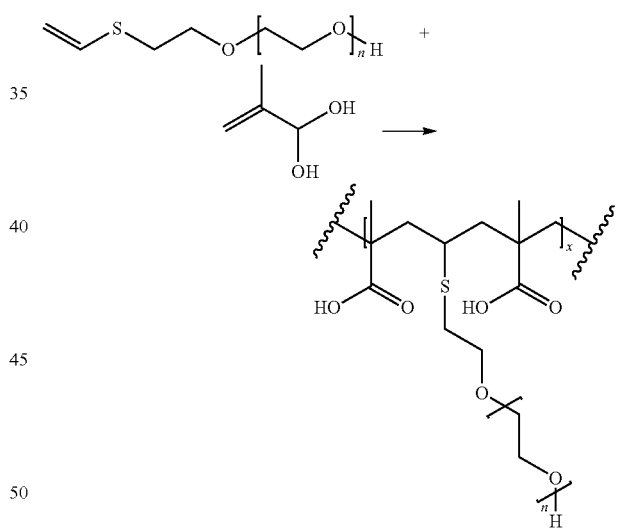

Example 4a

Copolymer of 87% by weight VME-24EO and 13% by weight Na methacrylate
Polymerization at pH 7.5-8.0 (azo starter), method (A)

57 g of water, 34.8 g of VME-24EO, a portion (1.4 g) of solution A (17.2 g of 30% methacrylic acid Na salt solution and 12 g of water) and a portion (2.0 g) of solution B (1.6 g of 2,2'-azobis[2-(2-imidazolin-2-yl)propane]dihydrochloride (Wako VA-44) and 38.4 g of water) were initially charged in a glass reactor equipped with stirrer, reflux condenser, thermometer, nitrogen line and addition lines. The initial charge was heated under nitrogen to 70° C. and the addition of the remaining amounts of solutions A and B was started, wherein solution A was added over 3 hours and solution B over 4 hours. The reaction mixture was then stirred at 70° C. for 2 h.

The results are summarized in table 3.

Example 4b

Copolymer of 82% by weight VME-23EO and 18% by weight Na methacrylate
Polymerization at pH 7.5-8.0 (peroxide starter), method (A)

70 g of water, 33 g of VME-23EO, a portion (2.1 g) of solution A (24 g of 30% methacrylic acid Na salt solution and 20 g of water) and a portion (0.8 g) of solution B (1.6 g (75% solution) of tert-butyl perpivalate and 14.4 g of isopropanol) were initially charged in a glass reactor equipped with stirrer, reflux condenser, thermometer, nitrogen line and addition lines. The initial charge was heated under nitrogen to 75° C. and the addition of the remaining amounts of solutions A and B was started, wherein solution A was added over 3 hours and solution B over 4 hours. The reaction mixture was then stirred at 75° C. for 2 h. Isopropanol was distilled off.

The results are summarized in table 3.

Example 4c

Copolymer of 87% by weight VME-23EO and 13% by weight Na methacrylate
Polymerization at pH 2.5-3.0 (peroxide starter), method (A)

70 g of water, 35 g of VME-23EO, a portion (2.0 g) of solution A (5.2 g of methacrylic acid dissolved in 36 g of water) and a portion (0.8 g) of solution B (1.6 g (75% solution) of tert-butyl perpivalate and 14.4 g of isopropanol) were initially charged in a glass reactor equipped with stirrer, reflux condenser, thermometer, nitrogen line and addition lines. The initial charge was heated under nitrogen to 75° C. and the addition of the remaining amounts of solutions A and B was started, wherein solution A was added over 3 hours and solution B over 4 hours. The reaction mixture was then stirred at 75° C. for 2 h. Isopropanol was distilled off.

The results are summarized in table 3.

Example 4d

Copolymer of 89% by weight VME-23EO and 11% by weight Na methacrylate
Polymerization at pH 7.5-8.0 (azo starter), method (B)

66 g of water, a portion (2.9 g) of solution A (35.6 g of VME-23EO, 4.4 g of methacrylic acid dissolved in 18 g of water) and a portion (1.9 g) of solution B (1.6 2,2'-azobis[2-(2-imidazolin-2-yl)propane]dihydrochloride (Wako VA-44) and 36 g of water) were initially charged in a glass reactor equipped with stirrer, reflux condenser, thermometer, nitrogen line and addition lines. The initial charge was heated under nitrogen to 70° C. and the addition of the remaining amounts of solutions A and B was started, wherein solution A was added over 3 hours and solution B over 4 hours. The reaction mixture was then stirred at 70° C. for 2 h.

The results are summarized in table 3.

Example 4e

Copolymer of 89% by weight VME-23EO and 11% by weight Na methacrylate
Polymerization at pH 7.5-8.0 (peroxide starter), method (B)

66 g of water, a portion (2.9 g) of solution A (35.6 g of VME-23EO, 4.4 g of methacrylic acid dissolved in 18 g of water) and a portion (1.9 g) of solution B (0.8 g (75% solution) of tert-butyl perpivalate and 36 g of isopropanol) were initially charged in a glass reactor equipped with stirrer, reflux condenser, thermometer, nitrogen line and addition lines. The initial charge was heated under nitrogen to 75° C. and the addition of the remaining amounts of solutions A and B was started, wherein solution A was added over 3 hours and solution B over 4 hours. The reaction mixture was then stirred at 75° C. for 2 h. Isopropanol was distilled off.

The results are summarized in table 3.

Comparative Example 4f

Copolymer of 87% by weight HBVE-23EO and 13% by weight Na methacrylate
Polymerization at pH 7.5-8.0 (azo starter), method (A)

Reaction scheme:

57.6 g of water, 35 g of HBVE-24EO, a portion (1.5 g) of solution A (17 g of 30% methacrylic acid Na salt solution and 12 g of water) and a portion (2.0 g) of solution B (1.6 g of 2,2'-azobis[2-(2-imidazolin-2-yl)propane]dihydrochloride (Wako VA-44) and 38.4 g of water) were initially charged in a glass reactor equipped with stirrer, reflux condenser, thermometer, nitrogen line and addition lines. The initial charge was heated under nitrogen to 70° C. and the addition of the remaining amounts of solutions A and B was started, wherein solution A was added over 3 hours and solution B over 4 hours. The reaction mixture was then stirred at 70° C. for 2 h.

The results are summarized in table 3.

Comparative Example 4g

Copolymer of 87% by weight HBVE-23EO and 13% by weight Na methacrylate
Polymerization at pH 7.5-8.0 (azo starter), method (B)

66 g of water, a portion (2.9 g) of solution A (35.6 g of VME-23EO, 4.4 g of methacrylic acid dissolved in 18 g of water) and a portion (1.9 g) of solution B (1.6 2,2'-azobis[2-(2-imidazolin-2-yl)propane]dihydrochloride (Wako VA-44) and 36 g of water) were initially charged in a glass reactor equipped with stirrer, reflux condenser, thermometer, nitrogen line and addition lines. The initial charge was heated under nitrogen to 70° C. and the addition of the remaining amounts of solutions A and B was started, wherein solution A was added over 3 hours and solution B over 4 hours. The reaction mixture was then stirred at 70° C. for 2 h.

The results are summarized in table 3.

Example 4h

Copolymer of 87% by weight VME-24EO and 13% by weight Na methacrylate
Polymerization at pH 7.5-8.0 (peroxide starter)

66 g of water, a portion (2.9 g) of solution A (35.6 g of VME-23EO, 4.4 g of acrylic acid dissolved in 18 g of water) and a portion (1.9 g) of solution B (0.8 g (75% solution) of tert-butyl perpivalate and 36 g of isopropanol) were initially charged in a glass reactor equipped with stirrer, reflux condenser, thermometer, nitrogen line and addition lines. The initial charge was heated under nitrogen to 75° C. and the addition of the remaining amounts of solutions A and B was started, wherein solution A was added over 3 hours and solution B over 4 hours. The reaction mixture was then stirred at 75° C. for 2 h. Isopropanol was distilled off.

The results are summarized in table 3.

temperature sensor, pH probe and $N_2$ inlet. 172.80 g of water and 103.38 g of VME-67 EO are added to the reactor. $N_2$ is then introduced and the oxygen displaced. The thermostat is set at T=75° C. and the reactor content is heated.

At ca. 60° C., 25.94 g of hydroxyethyl methacrylate phosphate (HEMA-P) in 137.12 g of water is added. A pH of ca. 1.0-1.5 is reached. Subsequently, 9.02 g of 50% NaOH are added thereto in order to establish a pH of ca. 3. On addition of the HEMA-P solution, the temperature falls down to 50° C. The reactor content is subsequently heated to 60° C. 1.32 g of Wako VA-044 (2,2'-azobis[2-(2-imidazolin-2-yl)propane]dihydrochloride) in 13.2 g of water are then added. After a reaction time of 3 h, the reactor content is cooled to 25° C.

The resulting yellowish slightly cloudy product has a pH of ca. 2.5 and a solids content of 30%. The mean molar mass of the polymer (Mw) is 29 000 g/mol. The polydispersity is 1.25. The conversion is ca. 75% of polymer (determination by GPC).

The results are summarized in table 4.

Example 5b

Copolymer of 84% by Weight VME-135EO and 16% by Weight Hydroxyethyl Methacrylate Phosphate The same apparatus was used as for example 5a.

172.80 g of water and 106.38 g of VME-135 EO are added to the reactor. $N_2$ is then introduced and the oxygen displaced. The thermostat is set at T=75° C. and the reactor content is heated. At ca. 60° C., 19.79 g of hydroxyethyl methacrylate phosphate (HEMA-P) in 104.6 g of water is added. A pH of ca. 1.0-1.5 is reached. Subsequently, 7.05 g of 50% NaOH are added thereto in order to establish a pH of ca. 3. On addition of the HEMA-P solution, the temperature falls down to 50° C. The reactor content is subsequently heated to 60° C. 1.26 g of Wako VA-044 (2,2'-azobis[2-(2-

TABLE 3

Results of examples 4a-4h

| No. | Macromonomer | Process | Initiator | Temp. [° C.] | pH | $M_n$ [g/mol] | $M_w$ [g/mol] | $M_w/M_n$ | Unreacted macromonomer [%]* |
|---|---|---|---|---|---|---|---|---|---|
| Example 4a | VME-24EO | (A) | 4% W-VA44 | 70 | 8.3 | 24789 | 33344 | 1.34 | — |
| Example 4b | VME-24EO | (A) | 4% perpivalate | 75 | 7.9 | 17980 | 41600 | 2.31 | — |
| Example 4c | VME-24EO | (A) | 4% perpivalate | 75 | 2.4 | 43381 | 68891 | 1.59 | — |
| Comparative example 4d | HBVE-24EO | (A) | 4% W-VA44 | 70 | 7.8 | 18408 | 24217 | 1.32 | — |
| Comparative example 4e | HBVE-24EO | (B) | 4% perpivalate | 75 | 8.8 | 17271 | 23080 | 1.34 | ~75 |
| Example 4f | VME-24EO | (B) | 4% perpivalate | 75 | 8.5 | 9054 | 20575 | 2.75 | ~48 |
| Comparative example 4g | HBVE-24EO | (B) | 4% W-VA44 | 70 | 8.4 | 16875 | 24364 | 1.44 | ~20 |
| Example 4h | VME-24EO | (B) | 4% W-VA44 | 70 | 8.6 | 7968 | 14725 | 1.85 | ~6 |

Example 5

Copolymerization of VME Alkoxylates with HEMA and HPMA Phosphate Compared to HBVE Alkoxylates

Example 5a

Copolymer of 80% by Weight VME-67EO and 20% by Weight Hydroxyethyl Methacrylate Phosphate The experimental apparatus consists of 1000 ml jacketed reactor, thermostat, stirring motor with propeller stirrer, imidazolin-2-yl)propane]dihydrochloride) in 11.3 g of water are then added. After a reaction time of 3 h, the reactor content is cooled to 25° C.

The results are summarized in table 4.

Beispiel 5c

Copolymer of 89% by Weight VME-135EO and 11% by Weight Hydroxyethyl Methacrylate Phosphate The same apparatus was used as for example 5a.

328.3 g of water and 202.12 g of VME-135 EO are added to the reactor. $N_2$ is then introduced and the oxygen displaced. The thermostat is set at T=75° C. and the reactor content is heated. At ca. 60° C., 25.06 g of hydroxyethyl methacrylate phosphate (HEMA-P) in 132.5 g of water are added. A pH of ca. 1.0-1.5 is reached. Subsequently, 8.90 g of 50% NaOH are added thereto in order to establish a pH of ca. 3. On addition of the HEMA-P solution, the temperature falls down to 50° C. The reactor content is subsequently heated to 60° C. 2.27 g of Wako VA-044 (2,2'-azobis[2-(2-imidazolin-2-yl)propane]dihydrochloride) in 21.6 g of water are then added. After a reaction time of 3 h, the reactor content is cooled to 25° C.

The results are summarized in table 4.

Example 5d

Copolymer of 92% by Weight VME-135EO and 8% by Weight Hydroxyethyl Methacrylate Phosphate The same apparatus was used as for example 5a.

328.3 g of water and 202.12 g of VME-135 EO are added to the reactor. $N_2$ is then introduced and the oxygen displaced. The thermostat is set at T=75° C. and the reactor content is heated. At ca. 60° C., 16.71 g of hydroxyethyl methacrylate phosphate (HEMA-P) in 88.31 g of water are added. A pH of ca. 1.0-1.5 is reached. Subsequently, 5.78 g of 50% NaOH are added thereto in order to establish a pH of ca. 3. On addition of the HEMA-P solution, the temperature falls down to 50° C. The reactor content is subsequently heated to 60° C. 2.19 g of Wako VA-044 (2,2'-azobis[2-(2-imidazolin-2-yl)propane]dihydrochloride) in 21.6 g of water are then added.

After a reaction time of 3 h, the reactor content is cooled to 25° C.

The results are summarized in table 4.

Example 5e

Copolymer of 84% by Weight VME-10PO-125EO and 16% by Weight Hydroxyethyl Methacrylate Phosphate The same apparatus was used as for example 5a.

328.3 g of water and 202.12 g of VME-10PO-125 EO are added to the reactor. $N_2$ is then introduced and the oxygen displaced. The thermostat is set at T=75° C. and the reactor content is heated. At ca. 60° C., 37.59 g of hydroxyethyl methacrylate phosphate (HEMA-P) in 198.7 g of water are added. A pH of ca. 1.0-1.5 is reached. Subsequently, 13.45 g of 50% NaOH are added thereto in order to establish a pH of ca. 3. On addition of the HEMA-P solution, the temperature falls down to 50° C. The reactor content is subsequently heated to 60° C. 2.4 g of Wako VA-044 (2,2'-azobis[2-(2-imidazolin-2-yl)propane]dihydrochloride) in 21.6 g of water are then added.

After a reaction time of 3 h, the reactor content is cooled to 25° C.

The results are summarized in table 4.

Example 5f

Copolymer of 84% by Weight VME-135EO and 16% by Weight Hydroxypropyl Methacrylate Phosphate The same apparatus was used as for example 5a.

328.3 g of water and 202.12 g of VME-135 EO are added to the reactor. $N_2$ is then introduced and the oxygen displaced. The thermostat is set at T=75° C. and the reactor content is heated. At ca. 60° C., 38.81 g of hydroxypropyl methacrylate phosphate (HPMA-P) in 198.7 g of water are added. A pH of ca. 1.0-1.5 is reached.

Subsequently, 11.5 g of 50% NaOH are added thereto in order to establish a pH of ca. 3. On addition of the HPMA-P solution, the temperature falls down to 50° C. The reactor content is subsequently heated to 60° C. 2.4 g of Wako VA-044 (2,2'-azobis[2-(2-imidazolin-2-yl)propane]dihydrochloride) in 21.6 g of water are then added.

After a reaction time of 3 h, the reactor content is cooled to 25° C.

The results are summarized in table 4.

Example 5g

Copolymer of 98% by Weight VME-135EO and 2% by Weight Maleic Anhydride

The same apparatus was used as for example 5a.

218.88 g of water and 134.75 g of VME-135 EO are added to the reactor. $N_2$ is then introduced and the oxygen displaced. The thermostat is set at T=75° C. and the reactor content is heated. At ca. 60° C., 2.67 g of maleic anhydride (MA) in 7.9 g of water are added. Subsequently, 2.68 g of 40% KOH are added thereto in order to establish a pH of ca. 3. On addition of the MA solution, the temperature falls down to 50° C. The reactor content is subsequently heated to 60° C. 1.37 g of Wako VA-044 (2,2'-azobis[2-(2-imidazolin-2-yl)propane]dihydrochloride) in 12.37 g of water are then added.

After a reaction time of 3 h, the reactor content is cooled to 25° C.

The results are summarized in table 4.

Comparative Example 5a

Copolymer of 84% by Weight HBVE-135EO and 16% by Weight Hydroxyethyl Methacrylate Phosphate The same apparatus was used as for example 5a.

217.15 g of water and 133.68 g of HBVE-135EO are added to the reactor. $N_2$ is then introduced and the oxygen displaced. The thermostat is set at T=75° C. and the reactor content is heated. At ca. 60° C., 25.72 g of hydroxyethyl methacrylate phosphate (HEMA-P) in 135.95 g of water are added. Subsequently, 9.13 g of 50% NaOH are added thereto in order to establish a pH of ca. 6.5. On addition of the HEMA-P solution, the temperature falls down to 50° C. The reactor content is subsequently heated to 60° C. 1.59 g of Wako VA-044 (2,2'-azobis[2-(2-imidazolin-2-yl)propane]dihydrochloride) in 11.34 g of water are then added.

After a reaction time of 3 h, the reactor content is cooled to 25° C.

The results are summarized in table 4.

Comparative Example 5c

Copolymer of 98% by Weight HBVE-135EO and 2% by Weight Maleic Anhydride

The same apparatus was used as for example 5a.

434.3 g of water and 267.37 g of HBVE-135EO are added to the reactor. $N_2$ is then introduced and the oxygen displaced. The thermostat is set at T=75° C. and the reactor content is heated. At ca. 60° C., 5.48 g of maleic anhydride (MA) in 28.62 g of water are added. Subsequently, 5.3 g of 40% KOH are added thereto in order to establish a pH of ca. 6.5. On addition of the MA solution, the temperature falls down to 50° C. The reactor content is subsequently heated to 60° C. 2.73 g of Wako VA-044 (2,2'-azobis[2-(2-imidazolin-2-yl)propane]dihydrochloride) in 24.55 g of water are then added. After a reaction time of 3 h, the reactor content is cooled to 25° C.

The results are summarized in table 4.

TABLE 4

Results of examples 5a to 5g and comparative examples 5a to 5c (*conversion determined by GPC)

| Example | Macromonomer | Weight ratio macromonomer/comonomer | $M_n$ [g/mol] | $M_w$ [g/mol] | PD | Solids content [% by wt.] | Conversion* [%] |
|---|---|---|---|---|---|---|---|
| Example 5a | VME-67EO | 80/20 (HEMA-P) | 22100 | 27400 | 1.24 | 30 | 93 |
| Example 5b | VME-135EO | 84/16 (HEMA-P) | 19000 | 25600 | 1.35 | 33 | 78 |
| Example 5c | VME 135EO | 89/11 (HEMA-P) | 19900 | 27600 | 1.39 | 32 | 82 |
| Example 5d | VME-135EO | 92/8 (HEMA-P) | 50593 | 91007 | 1.79 | 33 | 70 |
| Example 5e | VME-10PO-125EO | 84/16 (HEMA-P) | 55000 | 80300 | 1.46 | 31 | 81 |
| Example 5f | VME-135EO | 84/16 (HEMA-P) | 17100 | 21900 | 1.28 | 31 | 74 |
| Example 5g | VME-135EO | 98/2 (MSA) | 19700 | 25400 | 1.29 | 37 | 62 |
| Comparative example 5 a | HBVE-135EO | 84/16 (HEMA-P) | 32200 | 84600 | 2.63 | 31 | 6 |
| Comparative example 5 b | HBVE-135EO | 89/11 (HEMA-P) | 23900 | 34500 | 1.44 | 33 | 5 |
| Comparative example 5 c | HBVE-135EO | 98/2 (MA) | — | — | — | 37 | 0 |

Comparative Example 5b

Copolymer of 89% by Weight HBVE-135EO and 11% by Weight Hydroxyethyl Methacrylate Phosphate The same apparatus was used as for example 5a.

217.15 g of water and 133.68 g of HBVE-135EO are added to the reactor. $N_2$ is then introduced and the oxygen displaced. The thermostat is set at T=75° C. and the reactor content is heated. At ca. 60° C., 17.15 g of hydroxyethyl methacrylate phosphate (HEMA-P) in 90.64 g of water are added. Subsequently, 9.5 g of 50% NaOH are added thereto in order to establish a pH of ca. 6.5. On addition of the HEMA-P solution, the temperature falls down to 50° C. The reactor content is subsequently heated to 60° C. 1.51 g of Wako VA-044 (2,2'-azobis[2-(2-imidazolin-2-yl)propane]dihydrochloride) in 11.34 g of water are then added. After a reaction time of 3 h, the reactor content is cooled to 25° C.

The results are summarized in table 4.

Application Tests
Test Methods:

Spread test using polycarboxylate ether plasticizer based on VME ethoxylate compared to HBVE ethoxylate.

A mortar composed of 450 g of Heidelberg cement CEM I, 42.5 R, 1350 g of standard sand and 225 g of water (less the water to be added with the plasticizer) was prepared according to DIN EN 196-1. The plasticizer (between 0.1 and 0.3% by weight based on the cement) was added after 90 seconds during the mortar preparation, together with the antifoaming agent triisobutyl phosphate (7% by weight based on the dry weight of the plasticizer). After the addition, mixing was continued for 60 s. The mortar was then loaded into a conical metallic mold which was placed centrally on a jolting table at the origin of a rectangular coordinate system with two axes (units cm). Excess mortar was wiped off the upper edge and the mold lifted off such that a conical mortar cake remained on the spread table. After 15 strokes (upward strokes) by means of the jolting table, the diameter of the cake was determined along the axes. The greater the diameter of the mortar cake, the better the flow properties of the mortar. The measurement was repeated with the same mortar sample after 30, 60 and 90 minutes. The temperature was 23+/−1° C.

The polymers used in each case, amount thereof and test results are summarized in Table 5.

TABLE 5

Results of the performance tests

| No. | Process | Polymer No. | Type of polymer | pH during polymerization | $M_n$ [g/mol] | $M_w$ [g/mol] | $M_w/M_n$ | Amount of Polymer relative to cement [% by wt.] | Diameter after x min. [cm] | | | |
|---|---|---|---|---|---|---|---|---|---|---|---|---|
| | | | | | | | | | 1 min. | 30 min. | 60 min. | 90 min. |
| V1 | (A) | — | Blank sample without polymer | — | — | — | — | — | 17.65 | 15.7 | 14.95 | 13.35 |
| V2 | (A) | V2a | 89% HBVE-24EO, 11% AA | 2-3 | 1267 | 12459 | 9.83 | 0.12 | 19.55 | 17.2 | 15.4 | 15.4 |
| V3 | (A) | V2b | 89% HBVE-24EO, 11% AA | 2-3 | 1141 | 4366 | 3.82 | 0.12 | 19.3 | 17.5 | 16.8 | 14.85 |
| V4 | (A) | V2c | 89% HBVE-24EO, 11% AA | 2-3 | 1478 | 17994 | 12.2 | 0.12 | 19.55 | 17.6 | 16.75 | 15.7 |
| 1 | (A) | 2a | 89% VME-23EO, 11% AA | 2-3 | 6348 | 34566 | 5.44 | 0.12 | 20.7 | 18.55 | 16.75 | 15.9 |
| 2 | (A) | 2b | 89% VME-23EO, 11% AA | 2-3 | 6137 | 41648 | 6.78 | 0.12 | 21.15 | 18.25 | 17.2 | 16.45 |
| 3 | (A) | 2c | 89% VME-23EO, 11% AA | 2-3 | 6591 | 42874 | 6.5 | 0.12 | 21.05 | 18.35 | 16.85 | 16.25 |
| V5 | (A) | V2c | 89% HBVE-24EO, 11% AA | 2-3 | 1478 | 17994 | 12.2 | 0.24 | 21.1 | 19.45 | 18.4 | 16.3 |
| 4 | (A) | 2b | 89% VME-23EO, 11% AA | 2-3 | 6137 | 41648 | 6.78 | 0.24 | 26 | 22.2 | 19.6 | 18.35 |
| 5 | (A) | 2d | 85% VME-23EO, 11% AA | 2-3 | 4974 | 20834 | 4.18 | 0.115 | 20.55 | 18.35 | 17.55 | 16.65 |
| 6 | (A) | 2d | 85% VME-23EO, 11% AA | 7-8 | 4974 | 20834 | 4.18 | 0.23 | 23.15 | 19.45 | 18.4 | 17.5 |
| 7 | (B) | 3a | 89% VME-23EO, 11% AA | 2-3 | 27709 | 42697 | 2.7 | 0.1 | 29.3 | 24.9 | 22.25 | 21.3 |
| 8 | (B) | V3a | 86% HBVE-24EO, 14% AA | 8-9 | 12238 | 15404 | 1.26 | 0.12 | 21.1 | 18.7 | 17.5 | 16.25 |
| V6 | (B) | V3b | 86% HBVE-24EO, 14% AA | 7-9 | 18028 | 25349 | 1.41 | 0.12 | 22.5 | 19.1 | 17.3 | 16.6 |
| 9 | (B) | 3b | 89% VME-23EO, 11% AA | 2-3 | 23197 | 37150 | 2.7 | 0.1 | 28.05 | 23.15 | 22.25 | 19.55 |
| 10 | (B) | 3c | 97% VME-135EO, 3% AA | 8-10 | 15682 | 20930 | 1.33 | 0.11 | 19.2 | 16.8 | 15.65 | 15.15 |
| 11 | (B) | V3c | 94% HBVE-135EO, 6% AA | 7-9 | 36819 | 39428 | 1.07 | 0.11 | 19.3 | 16.9 | 16 | 15 |
| 12 | (B) | 3d | 97% VME-135EO, 3% AA | 8-10 | 18776 | 29705 | 1.58 | 0.11 | 19 | 16.95 | 15.95 | 15.1 |
| 13 | (A) | 4a | VME-24EO, MAS | 8-9 | 24789 | 33344 | 1.34 | 0.11 | 21.7 | 18.45 | 17.95 | 17.65 |
| 14 | (A) | 4b | VME-24EO, MAS | 8-9 | 17980 | 41600 | 2.31 | 0.11 | 27.3 | 21.85 | 18.60 | 16.45 |
| 15 | (A) | 4c | VME-24EO, MAS | 2-3 | 43381 | 68891 | 1.59 | 0.11 | 21.35 | 18.35 | 17.55 | 16.25 |
| V7 | (A) | V4d | HBVE-24EO, MAS | 7.8 | 18408 | 24217 | 1.32 | 0.11 | 19.7 | 18 | 17 | 16.25 |
| V8 | (B) | | HBVE-24EO, MAS | 8-9 | 14585 | 19709 | 1.35 | 0.11 | 19.5 | 17.2 | 16.65 | 16.35 |
| 16 | (B) | | VME-24EO, MAS | 8-9 | 27877 | 40371 | 1.45 | 0.11 | 21.85 | 18.75 | 17.6 | 16.85 |
| V9 | (B) | V4e | HBVE-24EO, MAS | 8-9 | 17271 | 23080 | 1.34 | 0.11 | 20.35 | 17.8 | 16.55 | 15.45 |
| 16 | (B) | 4f | VME-24EO, MAS | 8-9 | 9054 | 20575 | 2.75 | 0.11 | 20.95 | 17.70 | 16.75 | 15.80 |
| V10 | (B) | V4g | HBVE-24EO, MAS | 8-9 | 16875 | 24364 | 1.44 | 0.11 | 20.45 | 17.60 | 16.70 | 16.00 |
| 17 | (B) | 4h | VME-24EO, MAS | 8-9 | 7968 | 14725 | 1.85 | 0.11 | 20.15 | 17.50 | 16.30 | 15.85 |

Comments on the Performance Experiments

The examples in the table show that the experiments using the VME ethoxylates have a better effect with respect to the mortar plastification than the HBVE-based experiments.

In the blank experiment, the diameter of the mortar cake after 1 min was 17.65 cm. The addition of 0.12% of an HBVE-based plasticizer (comparative example V2) leads after 1 min to a mortar cake diameter of 19.55 cm. With the corresponding VME-based product (example 2), 21.15 cm are reached. The VME-based product is also better on doubling the concentration; 26 cm (experiment 4) are achieved with the VME-based product and only 21.1 cm with the HBVE-based product.

The experiments also show that better performance results are achieved with polymers prepared according to method (B) than with polymers prepared according to method (A): At an amount of 0.12% by weight, the best experiment with a VME-based product prepared according to method (A) gave 21.15 cm. In experiments 7 and 9, ca. 28 to 29 cm were achieved with a VME-based product prepared according to method (B) even though the amount of polymer, at 0.1% by weight, was lower than in experiment 2 (0.12% by weight).

Although we do not wish to be committed to a theory, it seems that the effect is due to the fact that the compounds (I) relatively easily self-polymerize due to their relatively high reactivity. Since the compounds (I) are initially charged in method (A) and the comonomers are added gradually, the formation of block structures is favored. Method (B), in which both monomers are added gradually, seems to lead to a more uniform incorporation of the VME monomers into the copolymer. A significantly better effect as concrete plasticizer can evidently thereby be achieved.

The invention claimed is:

1. An unsaturated compound of formula (I)

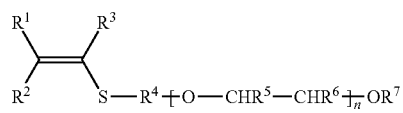

wherein
R$^1$, R$^2$, and R$^3$ are the same or different and are each independently H or CH$_3$,
R$^4$ is a linear or branched C$_1$-C$_{30}$-alkylene,
R$^5$ and R$^6$ are the same or different and are each independently selected from the group consisting of H, C$_1$-C$_{20}$-alkyl, C$_3$-C$_{15}$-cycloalkyl, aryl, —CH$_2$—O—CH$_1$-C$_{20}$-alkyl, and CH$_2$—O—C$_2$-C$_{20}$-alkenyl, where R$^5$ and R$^6$ may together form a C$_3$-C$_6$-alkylene,
R$^7$ is the same or different and is independently H, C$_1$-C$_4$-alkyl, or

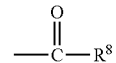

R$^8$ is C$_1$-C$_{22}$-alkyl or C$_2$-C$_{22}$-alkenyl, and
n is an integer from 21 to 200.

2. The unsaturated compound according to claim 1, wherein, in formula (I):
R$^4$ is a C$_2$-C$_4$-alkylene group,
R$^5$ and R$^6$ are the same or different and are each independently selected from the group consisting of H, —CH$_3$, —CH$_2$—CH$_3$, —C$_3$-C$_{11}$-alkyl, C$_{12}$-C$_{22}$-alkyl, phenyl, —CH$_2$—O—C$_1$-C$_{10}$-alkyl, and CH$_2$—O—C$_2$-C$_{10}$-alkenyl,
R$^7$ is or C$_1$-C$_4$-alkyl, and
n is 21 to 140.

3. The unsaturated compound according to claim 1, wherein the compound of formula (I) is an unsaturated compound of formula (Ia):

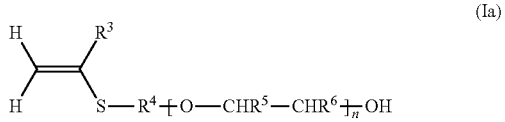

wherein:
R$^3$ is 1or methyl,
R$^4$ is a linear or branched C$_2$-C$_{10}$-alkylene group,
R$^5$ and R$^6$ are each independently H, methyl, or ethyl, with the proviso that the sum total of carbon atoms in the R$^5$ and R$^6$ residues per alkoxy group is in each case 0 to 2, and
n is 21 to 160.

4. The unsaturated compound according to claim 1, wherein the compound of formula (I) is an unsaturated compound of formula (Ib):

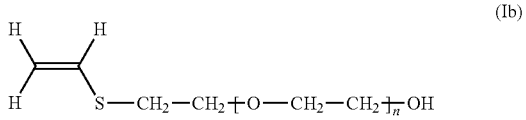

wherein n is 21 to 140.

5. The unsaturated compound according to claim 4, wherein, in formula (Ib), n is 21 to 30.

6. A mixture comprising the unsaturated compounds of formula (I) according to claim 1.

7. A polymer comprising the unsaturated compounds of formula (I) according to claim 1 as monomers.

8. A polymer comprising the unsaturated compounds of formula (Ia) according to claim 3 as monomers.

9. A polymer comprising the unsaturated compounds of formula (Ib) according to claim 4 as monomers.

10. The polymer according to claim 7, wherein at least one further monomer different from the unsaturated compounds of formula (I)is present in the polymer.

11. The polymer according to claim 10, wherein the at least one further monomer is at least one monoethylenically unsaturated monomer.

12. The polymer according to claim 11, wherein the monoethylenically unsaturated monomers are monomers comprising acid groups, where the acid groups may also be completely or partly neutralized.

13. The polymer according to claim 12, wherein the acid groups are selected from the group consisting of carboxylic acid groups, sulfonic acid groups, phosphoric acid groups, and phosphonic acid groups.

14. The polymer according to claim 13, wherein the polymer comprises at least one monomer having carboxylic acid groups selected from the group consisting of acrylic acid, methacrylic acid, (meth)acrylic anhydride, crotonic acid, maleic acid, maleic anhydride, fumaric acid, itaconic acid, mesaconic acid, citraconic acid, methylene malonic acid and salts thereof.

15. The polymer according to claim 13, wherein the polymer comprises at least one monomer having phosphoric acid groups or phosphonic acid groups selected from the group consisting of vinylphosphonic acid, an ester of hydroxyethyl (meth)acrylate with (poly)phosphoric acid, an ester of hydroxypropyl (meth)acrylate with (poly)phosphoric acid, an ester of hvdroxybutyl (meth)acrylate with (poly)phosphoric acid, monovinyl phosphate, allylphosphonic acid, monoallyl phosphate, 3-butenylphosphonic acid, mono-3-butenyl phosphate, mono(4-vinyloxybutyl) phosphate, mono(2-hydroxy-3-vinyloxypropyl) phosphate, mono(1-phosphonoxymethyl-2-vinyloxyethyl)phosphate, mono(3-allyloxy-2-hydroxypropyl) phosphate, mono [2-(allyloxy-1-phosphonoxymethylethyl)]phosphate, 2-hydroxy-4-vinyloxymethyl-1,3,2-dioxaphosphole, 2-hydroxy-4-allyloxymethyl-1,3,2-dioxaphosphole and salts thereof.

16. The polymer according to claim 13, wherein the polymer comprises at least one monomer having sulfonic acid groups selected from the group consisting of vinylsulfonic acid, 2-acrylamido-2-methylpropanesulfonic acid, 2-acrylamidomethyldodecylsulfonic acid, 2-(meth)acryloxyethanesulfonic acid, 3-(meth)acryloxypropanesulfonic acid, allyloxybenzenesulfonic acid, vinylbenzenesulfonic acid, vinyltoluenesulfonic acid, allylsulfonic acid, methallylsulfonic acid and salts thereof.

17. The polymer according to claim 11, wherein the at least one monoethylenically unsaturated monomer present is at least one selected from the group consisting of styrene, butadiene, methyl methacrylate, (meth)acrylate, ethyl acrylate, dibutyl maleate, methyl alpha-cyanoacrylate, acrylonitrile, acrylic acid, methacrylic acid, maleic acid (anhydride), itaconic acid, vinvlphosphonic acid, N-vinylpyrrolidone, N,N-dimethyl-N,N-diallylammonium chloride, acrylamide, vinylimidazole, vinyl alcohol, vinyl acetate, allylsulfonic acid, 2-acrylamido-2-methylpropanesulfonic acid, (iso)prenyl alkoxylate, (meth)allyl alkoxylate, and hydroxybutyl vinyl ether alkoxylate.

18. The polymer according to claim 17, wherein the at least one monoethylenically unsaturated monomer present is at least one selected from the group consisting of acrylic acid, methacrylic acid, (meth)acrylate, maleic acid (anhydride), (iso)prenyl alkoxylate, (meth)allyl alkoxylate, and hydroxybutyl vinyl ether alkoxylate.

19. The polymer according to claim 18, wherein the polymer consists of the unsaturated compounds of formula (I) and at least one monoethylenically unsaturated monomer selected from the group consisting of acid, methacrylic acid, (meth) acrylate, maleic acid (anhydride, (iso)prenyl alkoxylate, (meth)allyl alkoxylate, and hydroxybutyl vinyl ether alkoxylate as monomers.

20. The polymer according to claim 17, wherein the polymer consists of the unsaturated compounds of formula (I) and at least one monoethylenically unsaturated monomer selected from the group consisting of acrylic acid, methacrylic acid, and maleic acid (anhydride) as monomers.

21. The polymer according to claim 20, wherein the polymer consists of the unsaturated compounds of formula (I), acrylic acid, methacrylic acid, and maleic acid (anhydride) as monomers.

22. The polymer according to claim 7, wherein from 5 to 99.9% by weight of the unsaturated compounds of formula (I) are present in the polymer, based on the total amount of monomers.

23. The polymer according to claim 11, comprising, in each case based on a total amount of monomers:
from 5 to 99.9% by weight of the unsaturated compounds of formula (I); and from 95 to 0.1% by weight of the at least one monoethylenically unsaturated monomer.

24. The polymer according to claim 18, comprising, in each case based on a total amount of monomers:

from 5 to 99.9% by weight of the unsaturated compounds of formula (I); and from 95 to 0.1% by weight of the at least one monoethylenically unsaturated monomer.

25. The polymer according to claim 7, wherein the number-average molecular weight $M_n$, of the polymers is 1,000 g/mol to 1,000,000 g/mol.

26. The polymer according to claim 7, wherein the number-average molecular weight $M_n$ of the polymers is 5000 g/mol to 100,000 g/mol.

27. A method for preparing the polymer according to claim 7, wherein the unsaturated compounds of formula (I) and optionally at least one further monomer are subjected to free-radical polymerization.

28. The method according to claim 27, wherein the method is a copolymerization in which the unsaturated compounds of formula (I) and at least one further monoethylenically unsaturated monomer are subjected to free-radical polymerization.

29. The method according to claim 28, wherein the further monoethylenically unsaturated monomers are monomers comprising acid groups, ere he acid groups may also be completely or partly neutralized.

30. The method according to claim 29, wherein the acid groups are selected from the group consisting of carboxylic acid groups, sulfonic acid groups, phosphoric acid groups, and phosphoric acid groups.

31. The method according to claim 27, wherein the unsaturated compounds of formula (I) are unsaturated compounds of formula (Ia):

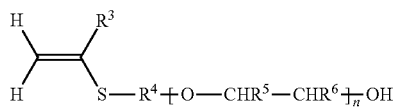

(Ia)

wherein:
$R^3$ is H or methyl,
$R^4$ is a linear or branched $C_2$-$C_{10}$-alkylene group,
$R^5$ and $R^6$ are each independently H, methyl, or ethyl, with the proviso that the sum total of carbon atoms in the $R^5$ and $R^6$ residues per alkoxy group is in each case 0 to 2, and
n is 21 to 160.

32. The method according to claim 27, wherein the unsaturated compounds of formula (I) are unsaturated compounds (Ib):

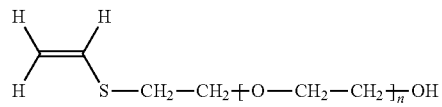

(Ib)

wherein n is 21 to 140.

33. The method according to claim 27, wherein the free-radical polymerization is carried out in aqueous solution.

34. The method according to claim 33, wherein the pH in the course of the polymerization is 1 to 6.

35. The method according to claim 33, wherein the pH in the course of the polymerization is 1 to 3.

36. The method according to claim 28, wherein the free-radical polymerization is carried out b initially charging a portion of the unsaturated compounds of formula (I), (Ia) or (Ib), a portion of the further monomers and also a portion of a polymerization initiator in a reactor, and gradually metering into the polymerization reactor the remaining amounts of the unsaturated compounds of formula (I), (Ia) or (Ib), the further monomers and also the polymerization initiator:

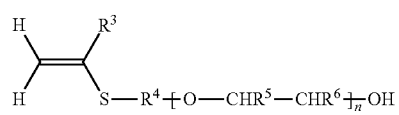

(Ia)

wherein:
$R^3$ is H or methyl,
$R^4$ is a linear or branched $C_2$-$C_{10}$-alkylene group,
$R^5$ and $R^6$ are each independently H, methyl, or ethyl, with the proviso that the sum total of carbon atoms in the $R^5$ and $R^6$ residues per alkoxy group is in each case 0 to 2, and
n is 21 to 160;

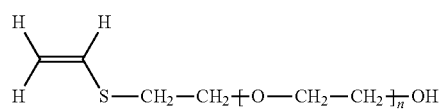

(Ib)

wherein n is 21 to 140.

37. The method according to claim 36, wherein the amount of monomers initially charged does not exceed 25% by weight of the total amount of the monomers.

38. A cement additive, grinding aid in the production of cement, concrete plasticizer, additive to hydraulic binders, reactive plasticizer for preparing plastics, rubber or latex, associative thickener and/or antioxidant, comprising the polymer according to claim 7.

39. A mixture comprising the polymer according to claim 7.

\* \* \* \* \*

UNITED STATES PATENT AND TRADEMARK OFFICE
CERTIFICATE OF CORRECTION

Page 1 of 2

PATENT NO. : 10,323,107 B2
APPLICATION NO. : 15/032916
DATED : June 18, 2019
INVENTOR(S) : Maitro-Vogel et al.

It is certified that error appears in the above-identified patent and that said Letters Patent is hereby corrected as shown below:

In the Specification

Column 1, Line 23, "C2- to C4-alkylene" should read -- $C_2$- to $C_4$-alkylene --.

Column 2, Line 26, "R4 is a linear" should read -- $R^4$ is a linear --.

Column 3, Line 33, "2-methyl-4-pentetenyl," should read -- 2-methyl-4-pentenyl, --.

Column 4, Lines 36-43 (approx.),

" 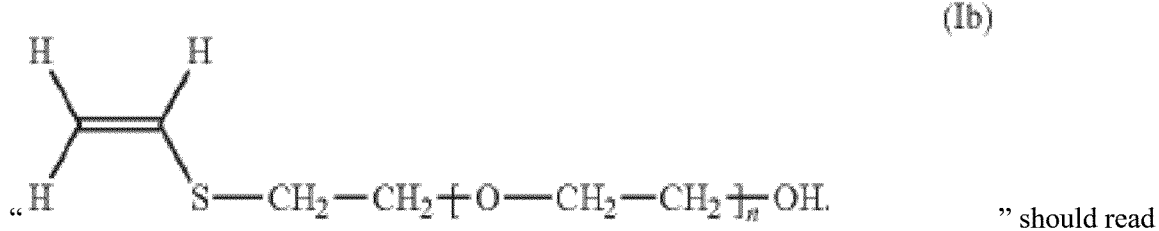 " should read

-- 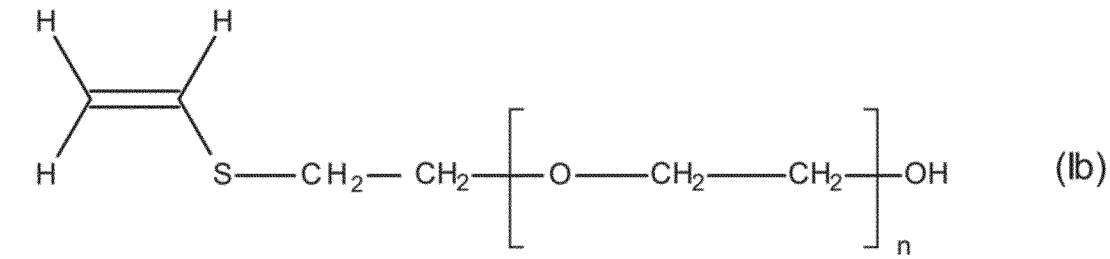 --.

Column 11, Line 11, "Mn may be," should read -- $M_n$ may be, --.

Column 15, Line 38, "rate 0.5 ml/min)." should read -- rate 0.5 ml/min. --.

Column 16, Line 8, "KOH/g)" should read -- KOH/g). --;

Signed and Sealed this
Seventh Day of July, 2020

Andrei Iancu
*Director of the United States Patent and Trademark Office*

Line 67, "by weight" should read -- by weight. --.

Column 17, Line 26, "by weight" should read -- by weight. --;
    Line 52, "KOH/g)" should read -- KOH/g). --.

Column 18, Line 13, "(theory 28.8)" should read -- (theory 28.8). --;
    Line 41, "by weight" should read -- by weight. --;
    Line 67, "by weight" should read -- by weight. --.

Column 19, Line 26, "by weight" should read -- by weight. --;
    Line 51, "polymerization" should read -- polymerization. --.

Column 24, Line 62, "HBVE-24 EO," should read -- HBVE-24EO, --.

Column 25, Line 9, "HBVE-67 EO," should read -- HBVE-67EO, --;
    Line 12, "HBVE-135 EO," should read -- HBVE-135EO, --;
    Line 57, "18 g of water)" should read -- 18 g of water --.

Column 28, Line 11, Table 2, "[g/mol" should read -- [g/mol] --.

Column 31, Line 40, Table 3, "[g/mol)" should read -- [g/mol] --;
    Line 40, Table 3, "[g/mol)" should read -- [g/mol] --.

In the Claims

Column 38, Claim 1, Line 61, "$R^8$ is $C_1$-$C_{22}$-alkyl" should read -- $R^8$ is $C_1$-$C_{22}$-alkyl --.

Column 39, Claim 2, Line 4, "$R^7$ is or" should read -- $R^7$ is H or --;

Column 39, Claim 3, Line 18, "$R^3$ is 1or" should read -- $R^3$ is H or --;

Column 39, Claim 10, Line 49, "(I)is" should read -- (I) is --.

Column 40, Claim 15, Line 7, "hvdroxybutyl" should read -- hydroxybutyl --;

Column 40, Claim 17, Line 32, "vinvlphosphonic" should read -- vinylphosphonic --;

Column 40, Claim 19, Line 47, "acid," should read -- acrylic acid, --;
    Line 48, "(anhydride," should read -- (anhydride), --.

Column 41, Claim 29, Line 29, "ere he acid" should read -- where the acid --;

Column 41, Claim 30, Line 35, "phosphoric" should read -- phosphonic --.

Column 42, Claim 36, Line 17, "out b initially" should read -- out by initially --.